(12) United States Patent
Engqvist

(10) Patent No.: US 11,202,871 B2
(45) Date of Patent: Dec. 21, 2021

(54) DEVICES FOR EVAPORATION AND INHALATION OF ACTIVE AGENTS

(71) Applicant: Emplicure AB, Uppsala (SE)

(72) Inventor: Håkan Engqvist, Uppsala (SE)

(73) Assignee: EMPLICURE AB, Uppsala (CH)

( * ) Notice: Subject to any disclaimer, the term of this patent is extended or adjusted under 35 U.S.C. 154(b) by 189 days.

(21) Appl. No.: 16/080,881

(22) PCT Filed: Feb. 28, 2017

(86) PCT No.: PCT/GB2017/050531
§ 371 (c)(1),
(2) Date: Aug. 29, 2018

(87) PCT Pub. No.: WO2017/149287
PCT Pub. Date: Sep. 8, 2017

(65) Prior Publication Data
US 2019/0038553 A1    Feb. 7, 2019

(30) Foreign Application Priority Data

Feb. 29, 2016 (GB) ..................................... 1603463
Feb. 21, 2017 (GB) ..................................... 1702805

(51) Int. Cl.
*A61M 15/00* (2006.01)
*A24F 40/42* (2020.01)
(Continued)

(52) U.S. Cl.
CPC .............. *A61M 15/00* (2013.01); *A24F 40/42* (2020.01); *A61K 9/0078* (2013.01); *A61K 9/143* (2013.01);
(Continued)

(58) Field of Classification Search
CPC ...... A61K 9/0073; A61K 9/0078; A61K 9/12; A61K 9/143; A61K 31/465; A61K 31/485;
(Continued)

(56) References Cited

U.S. PATENT DOCUMENTS 4,303,083 A    12/1981  Burruss, Jr.
5,318,779 A    6/1994   Hakamatsuka
(Continued)

FOREIGN PATENT DOCUMENTS

CN    104886785    9/2015
CN    205337599    6/2016
(Continued)

OTHER PUBLICATIONS

Reddit, Safe to Vape contents of advil liquid gels?, 2014, 1 page, https://www.reddit.com/r/shitty_ecr/comments/2aq7b8/safe_to_vape_contents_of_advil_liquid_gels/. (Year: 2014).*

(Continued)

*Primary Examiner* — Trevor Love
(74) *Attorney, Agent, or Firm* — Pabst Patent Group LLP

(57) ABSTRACT

There is provided an inhalation device for delivering a deliverable agent in the form of an aerosol or vapour to a user. The device comprises a solid, porous carrier material having a defined porosity, and a deliverable agent located within the pores of the carrier material. The device is operable to heat the carrier material and vaporise the deliverable agent. Deliverable agents that may be delivered to the user include active pharmaceutical ingredients. Suitable materials for the porous carrier material include chemically bonded ceramic materials and geopolymeric materials.

14 Claims, 17 Drawing Sheets

(51) Int. Cl.
| | |
|---|---|
| *A61P 25/34* | (2006.01) |
| *A61P 25/04* | (2006.01) |
| *A61K 31/465* | (2006.01) |
| *A61K 31/485* | (2006.01) |
| *A61M 16/10* | (2006.01) |
| *A61K 9/00* | (2006.01) |
| *A61K 9/14* | (2006.01) |
| *A61M 11/04* | (2006.01) |
| *A24F 40/465* | (2020.01) |
| *G05D 23/24* | (2006.01) |

(52) U.S. Cl.
CPC .......... *A61K 31/465* (2013.01); *A61K 31/485* (2013.01); *A61M 15/0001* (2014.02); *A61M 15/0045* (2013.01); *A61M 16/109* (2014.02); *A61P 25/04* (2018.01); *A61P 25/34* (2018.01); *A24F 40/465* (2020.01); *A61M 11/042* (2014.02); *A61M 2205/0211* (2013.01); *G05D 23/24* (2013.01)

(58) Field of Classification Search
CPC ................ A61M 11/042; A61M 15/00; A61M 15/0045; A61M 15/0001; A61M 15/0046; A61M 16/109; A61M 2202/0241; A61M 2205/0211; A61M 2205/3653; A61P 25/04; A61P 25/34; A61P 29/00; G05D 23/24
See application file for complete search history.

(56) References Cited

U.S. PATENT DOCUMENTS

| | | | |
|---|---|---|---|
| 9,016,274 | B1 | 4/2015 | White |
| 2003/0118641 | A1 | 6/2003 | Maloney |
| 2005/0163856 | A1 | 7/2005 | Maloney |
| 2006/0165787 | A1 | 7/2006 | Moerck |
| 2013/0220314 | A1 | 8/2013 | Bottom |
| 2014/0014126 | A1 | 1/2014 | Peleg |
| 2014/0202477 | A1 | 7/2014 | Qi |
| 2014/0238422 | A1 | 8/2014 | Plunkett |
| 2015/0059780 | A1 | 3/2015 | Davis |
| 2015/0074554 | A1 | 3/2015 | Sasaki |
| 2015/0075546 | A1 | 3/2015 | Kueny, Sr. |
| 2015/0209530 | A1 | 7/2015 | White |
| 2015/0359262 | A1 | 12/2015 | Liu |
| 2017/0065000 | A1 | 3/2017 | Sears |
| 2017/0231286 | A1* | 8/2017 | Borkovec ................. B65B 7/28 131/329 |
| 2017/0239229 | A1 | 8/2017 | Bredenberg |

FOREIGN PATENT DOCUMENTS

| | | |
|---|---|---|
| CN | 105755434 | 7/2016 |
| EP | 947489 | 10/1999 |
| WO | 9930760 | 6/1999 |
| WO | 9944448 | 9/1999 |
| WO | 2006017336 | 2/2006 |
| WO | 2006096544 | 9/2006 |
| WO | 2007131449 | 11/2007 |
| WO | 2007141668 | 12/2007 |
| WO | 2008118096 | 10/2008 |
| WO | 2008142572 | 11/2008 |
| WO | 2010128300 | 11/2010 |
| WO | 2011146174 | 11/2011 |
| WO | 2012032337 | 3/2012 |
| WO | 2013020220 | 2/2013 |
| WO | 2013060784 | 5/2013 |
| WO | 2015177252 | 11/2015 |
| WO | 2016142705 | 9/2016 |

OTHER PUBLICATIONS

Lasserre and Bajpai, "Ceramic drug-delivery devices", Crit Rev Ther Drug Carrier Syst., 15(1):1-56 (1998).
Byrne and Deasy, "Use of porous aluminosilicate pellets for drug delivery", J. of Microencapsulation: Micro and Nanocarriers, 22(4):423-237 (2008).
Callahan-Lyon, "Electronic cigarettes: human health effects",. Tob Contro., Supp 2:ii36-ii40 (2014).
Chae, et al., "Porosity control of porous silicon carbide ceramics", J. Eur. Ceramic Soc., 29(13):2867-72 (2009).
International Search Report for PCT/GB2017/050531 dated May 31, 2017.
International Search Report for PCT/GB2017/050533 dated May 31, 2017.
Kennedy, "Porous Metals and Metal Foams Made from Powders" Powder Metallurgy, 2:31-48 (2012).
Lee, "The Mechanical Properties of PMMA Bone Cement", The Well-Cemented Total Hip Arthroplasty, Basic Science, 3(2): 60-66 (2005).
Levis and Deasy, "Use of coated microtubular halloysite for the sustained release of diltiazem hydrochloride and propranolol hydrochloride", Int. J. Pharm., 253:145-57 (2003).
Mitchell, "Oral Dosage Forms That Should Not be Crushed", Institute for Safe Medical Practices, 1-16 http://www.ismp.org/Tools/DoNotCrush.pdf (2014).
Rimoli, et al., "Synthetic zeolites as a new tool for drug delivery", J Biomed. Mater. Res., 87(1):156-64 (2008).
Science of Concrete (http://iti.northwestern.edu/cement/monograph/Monograph7_2.html).
Stevenson et al., "Relationships between composition, structure and strength of inorganic polymers", J. Mater. Sci., 40(8):2023-36 (2005).
Subia, et al., Biomaterial Scaffold Fabrication Techniques for Potential Tissue Engineering Applications, Tissue Engineering, (2010).
Yu, et al., "On the High Pure Alumina Composite powder fo Sintering at 1400° C., A Preliminary Ivestigation", Key Engineering Materials, 313:59-62 (2006).
Zheng, et al., "Preparation of geopolymer precursors by sol-gel method and their characterization", J. Material Sci., 44:3991-6 (2009).
Beaudoin, et al., "5-Hydration, Setting and Hardening of Portland Cement", Lea's Chemistry of Cement and Concrete (Fifth Edition)157-250 (2019). Abstract only.
Bullard, et al., "Mechanisms of Cement Hydration", Cement and Concrete Research, 51 pages (2011).
Fontaine, et al., "New Calcium Carbonate-Based Cements for Bone Reconstruction", Key Engineering Materials, 5 pages (2005).
Garcia, et al., "Ibuprofen, a traditional drug that may impact the course of COVID-19 new effective formulation in nebulizable solution", Medical Hypotheses, 144:110079 (2020).
Gibney, "Inhaled ibuprofen could help patients with CF", FiercePharma, (https://www.fiercepharma.com/drug-delivery/inhaled-ibuprofen-could-help-patients-cf) (2016).
Hajek, et al., "A Randomized Trial of E-Cigarettes versus Nicotine-Replacement Therapy", N. Engl. J. Med., 380:629-37 (2019).
Hermansson, "Nanostructured ceramics", Monitoring and Evaluation of Biomaterials and their Performance in Vivo, 1:3-18 (2017).
Imitrex Nasal Spray—Prescribing Information Leaflet, 28 pages, (GSK; Dec. 2017).
International Search Report for corresponding PCT application PCT/GB2018/052554 dated Nov. 20, 2018.
Kohobhange, et al., "Thermal decomposition of calcium carbonate (calcite polymorph) as examined by in-situ high-temperature X-ray powder diffraction", J. of Phys, and Chem. of Solids, 134:21-28 (2019).
Lindgren, et al., "The effect of inhaled clonidine in patients with asthma", Am. Rev. Respir. Dis., 134(2):266-9 (1986). (Abstract only).
Myszka, et al., "Mechanical improvement of calcium carbonate cements by in situ HEMA polymerization during hardening", J. Mater. Chem. B., 7:3403-3411 (2019).

(56) References Cited

OTHER PUBLICATIONS

Ng, et al., "Hydrated Cement", Waste and Supplementary Cementitious Materials In Concrete, 2018, retrieved from https://www.sciencedirect.com/topics/engineering/hydrated-cement (2018).

Onischuk, et al., "Analgesic Effect from Ibuprofen Nanoparticles Inhaled by Male Mice", Journal of Aerosol Medicine and Pulmonary Drug Delivery, vol. 22(1):1-9 (2009).

Texas A&M University, "Breathing in a Cure: Inhalable Ibuprofen on the Horizon", (www.sciencedaily.com/releases/2016/07/160701121354.htm) (2016).

Wagh, "Chapter—1 Introduction to Chemically Bonded Ceramics", Chemically Bonded Phosphate Ceramics (Second Edition), 1:4-16 (2016).

Website from UK Government National Health Service (https://www.nhs.uk/conditions/stop-smoking-treatments/) (2020).

Zoulgami, et al., "Synthesis and physico-chemical characterization of a polysialate-hydroxyapatite composite for potential biomedical application", Eur. Phys. J. AP, 19:173-9 (2002).

* cited by examiner

DEVICES FOR EVAPORATION AND INHALATION OF ACTIVE AGENTS

CROSS REFERENCE TO RELATED APPLICATIONS

This is a National phase application of International Application No. PCT/GB2017/050531 filed Feb. 28, 2017, which claims the benefit of Great Britain Application GB 1702805.1 filed Feb. 21, 2017, and of Great Britain Application GB 1603463.9 filed Feb. 29, 2016, which are hereby incorporated by reference in their entirety.

FIELD OF THE INVENTION

The invention relates to new inhalation devices that enable a deliverable agent, such as an active pharmaceutical ingredient, to be delivered in the form of an aerosol or vapour to a user through the use of a porous carrier material. Said devices may be useful in effecting delivery of controlled quantities of the deliverable agent to the user.

BACKGROUND

The listing or discussion of an apparently prior-published document in this specification should not necessarily be taken as an acknowledgement that the document is part of the state of the art or is common general knowledge.

Active agents may be delivered to recipients through the use of inhalation devices, which evaporate the active agent during use and allow it to be inhaled. Such systems are increasingly being used in the form of e-cigarettes for the delivery of vaporised nicotine to users. See, for example, international patent application WO 99/44448, US patent applications 2014/0202477 and 2014/0014126, and Callahan-Lyon P. Tob Control; 2014;23:ii36-ii40.

Evaporation devices typically comprise a chamber containing active ingredients in a dissolved or liquid form, together with a heating device for vaporising the liquid. The heating device, which may be a heating element, is generally positioned within the inhalation device so that it can directly heat an evaporation carrier containing a portion of the active ingredient, rather than the reservoir of active ingredient. The evaporation carrier lies partially submerged in the reservoir and draws the liquid from the reservoir by wicking (capillary action) towards the heating element at which point it is vaporised in order for it to be inhaled.

US patent application 2015/0209530 describes an inhalation device in which the substance to be delivered (either an active pharmaceutical ingredient or nicotine) is provided in the form of a paste before being coated onto a carrier material and allowed to dry. The dried paste and carrier material are then heated within the device to evaporate the active pharmaceutical ingredient or nicotine and allow it to be inhaled by the user. U.S. Pat. No. 4,303,083 also discloses a device for vaporising a volatile compound through heating the compound in liquid form.

Known inhalation devices, including so-called electronic cigarette ("e-cigarette") devices, often suffer from a number of problems, including providing an unpleasant taste to the user if the device is heated dry (i.e. when the volatile agent has run out). In addition, many of the additives provided in the liquids used therein are harmful and can cause health problems. For example, propylene glycol, vegetable glycerin and polyethene glycol are known to produce compounds such as formaldehyde and acetaldehyde under certain conditions, and such residues may be inhaled as a result of the heating process. Control of dosing is also difficult to achieve which can lead to excessive or imprecise dosing to patients.

The handling of large amounts of pure or concentrated nicotine presents a variety of practical difficulties, particularly for end users. Devices, including e-cigarettes, which contain a reservoir of liquid or which must be filled via a connection to an external reservoir can also suffer from problems relating to leakage and spillage of the liquid contents during use and/or filling. There is therefore a need to provide devices in which such difficulties are minimised.

Opioids are widely used in medicine as analgesics, for example in the treatment of patients with severe pain, chronic pain or to manage pain after surgery. Indeed, it is presently accepted that, in the palliation of more severe pain, no more effective therapeutic agents exist.

The term "opioid" is typically used to describe a drug that activates opioid receptors, which are found in the brain, the spinal chord and the gut. Three classes of opioids exist:

(a) naturally-occurring opium alkaloids. These include morphine and codeine;

(b) compounds that are similar in their chemical structure to the naturally occurring alkaloids. These so-called semi-synthetics are produced by chemical modification of the latter and include the likes of diamorphine (heroin), oxycodone and hydrocodone; and (c) truly synthetic compounds such as fentanyl and methadone. Such compounds may be completely different in terms of their chemical structures to the naturally-occurring compounds.

Of the three major classes of opioid receptors ($\mu$, $\kappa$ and $\delta$), the opioids' analgesic and sedative properties mainly derive from agonism at the $\mu$ receptor.

Opioid analgesics are used to treat severe, chronic cancer pain, often in combination with non-steroid anti-inflammatory drugs (NSAIDs), as well as acute pain (e.g. during recovery from surgery and breakthrough pain). Further, their use is increasing in the management of chronic, non-malignant pain.

In the design of formulations containing extremely potent drugs, such as opioids, the dosing must be precise and the risk for "dose dumping" has to be eliminated in view of the risk of severe and, on occasions, lethal side effects. Secondly, in some instances, patients may misuse their opioid medication, e.g. by willfully (and sometimes unintentionally) tampering with a formulation in order to get more immediate absorption of opioid and a more rapid pain relieving effect. Thirdly, a perennial problem with potent opioid analgesics such as fentanyl is one of abuse by drug addicts. Addicts often apply innovative techniques in their abuse of pharmaceutical formulations, for example by way of one or more of the following processes:

(a) extracting a large quantity of active ingredient from that formulation using an appropriate eluent, such as an acid and/or alcohol, to form a solution, which is then injected intravenously. With most commercially-available pharmaceutical formulations, this can be done relatively easily, which renders them unsafe or "abusable";

(b) heating (and then smoking);

(c) crushing of tablet (and then snorting); and/or (d) in the case of a patch, making a tea (and then drinking).

Thus, there is a clear unmet clinical need for an effective pharmaceutical formulation that is capable of treating e.g. severe pain via the delivery of a controlled quantity of active ingredients (such as opioid analgesics) in a simple manner to patients that experience difficulty swallowing, whilst at the same time minimising the possibility of dose dumping, misuse by opioid treated patients and/or abuse by addicts.

One solution to these problems that has been suggested is the incorporation of the active substance into a polymer matrix (see e.g. US2003/0118641 and US2005/0163856), which allows for the slow release of the active substance. However, this solution is not adequate as the drug abuser could either liberate the active substance from the polymer matrix by co-mixing with a solvent (either prior to ingestion, or the solvent may be co-ingested with the polymer matrix/ active substance) or by crushing the polymer matrix.

Delivery of certain opioids to patients via inhalation is also desirable, however providing an abuse-deterrent formulation which is capable of both storing and releasing the opioid only when required by the end user is very difficult.

Ceramics are becoming increasingly useful to the medical world, particularly in view of the fact they are durable and stable enough to withstand the corrosive effect of body fluids.

Ceramics are also known to be of potential use as fillers or carriers in controlled-release pharmaceutical formulations. See, for example, EP 947 489 A, U.S. Pat. No. 5,318,779, WO 2008/118096, Lasserre and Bajpai, *Critical Reviews in Therapeutic Drug Carrier Systems*, 15, 1 (1998), Byrne and Deasy, *Journal of Microencapsulation*, 22, 423 (2005) and Levis and Deasy, *Int. J. Pharm.*, 253, 145 (2003).

In particular, Rimoli et al, *J. Biomed. Mater. Res.*, 87A, 156 (2008), US patent application 2006/0165787 and international patent applications WO 2006/096544, WO 2006/017336 and WO 2008/142572 all disclose various ceramic substances for controlled release of active ingredients, with the latter two documents being directed in whole or in part to opioid analgesics, with the abuse-resistance being imparted by the ceramic structures' mechanical strength.

DISCLOSURE OF THE INVENTION

According to a first aspect of the invention, there is provided a device for delivering a deliverable agent in the form of an aerosol or vapour to a user, comprising a solid, porous carrier material and a deliverable agent located within the pores of the carrier material. The porosity of the carrier material should be at least 10%. The device is further configured such that it is operable to heat the carrier material and thereby vaporise the deliverable agent.

Devices comprising such features are hereinafter referred to together as "the devices of the invention". They may also be referred to herein as "inhalation devices".

We have advantageously found that devices of the invention provide for release of a deliverable agent (e.g. an active pharmaceutical ingredient) in the form of an aerosol or a vapour (i.e. a gas) so as to allow a controllable quantity of the deliverable agent to be received by a subject via inhalation. The deliverable agent is a substance (or a mixture of substances) that may be delivered to an individual in order to provide a therapeutic effect.

In embodiments of the present invention, the deliverable agent is typically an active pharmaceutical ingredient.

The size of the pores in the carrier material should be chosen to enable the carrier material to effectively store a sufficient quantity of the deliverable agent for extended period of time with minimal loss under ambient conditions. This can be typically achieved using a carrier material with a porosity of at least 10%.

Typically, a high porosity is required for carrier materials that are used in the inhalation devices of the present invention. A minimum porosity of about 10% (by volume) is preferred for the carrier material used in the present invention. In a particular embodiment, the carrier material has a porosity of from about 10% to about 90%, such as from about 20% to about 70% (more preferably from about 30% to about 60%). Stronger materials may be suited to having a higher porosity. For example, metals may be particularly suitable for use with a porosity, which ranges from about 10% to about 90%, preferably from about 30% to about 80%. In embodiments in which the carrier material is based on a ceramic material or a geopolymeric material, the porosity may be from about 10% to about 90%, preferably from about 30% to about 70%, and more preferably from about 30% to about 60%. Control of the porosity of the carrier material is important as this ensures that controlled delivery of the deliverable agent to the user may be achieved.

Control of the pore size in the carrier material is also desirable in order to improve the controlled release characteristics of the devices of the invention. The pore size (e.g. an average internal dimension) of the carrier material should be sufficiently small to avoid rendering the carrier material too weak, and sufficiently large to ensure that the pores can receive the deliverable agent. In one embodiment, the average pore size is not larger than about 500μηι, and is preferably below about 200μηι. The average pore size may be as low as 0.5 nm (for so-called "micropores", as described in the Science of Concrete (Infrastructure Technology Institute (ITI), Northwestern University website). Voids with smaller dimensions are generally classified as interlayer spaces. A typical pore size distribution for hardened cement encompasses a large range, extending from as small as 0.5 nm (or possibly less) to about 10 μm in diameter. The larger pores, ranging from 10 nm to 10 μm, are the residual unfilled spaces between cement grains, and may also be defined as capillary pores. The finest pores range from approximately 0.5 nm to 10 nm. These are often called gel pores since they constitute the internal porosity of (for example) a calcium silicate hydrate gel phase. In one embodiment, the minimum average pore size may be about 0.5 nm, though it may be about 10 nm and is preferably about 0.10 μm. However, in some embodiments, the minimum pore size may be about 0.2 μm, such as about 0.25 μm. Thus in a preferred embodiment, the average pore size in the solid, porous material is from about 0.1 μm to about 500 μm or more preferably from about 0.2 μm to about 200 μm. Average pore sizes may be measured by methods known to the skilled person, for example the mercury intrusion method, the BET (Brunauer, Emmet, and Teller) method, and N2-adsorption techniques.

It is not necessary for the carrier material to be able to transmit air throughout the entire porous structure. In preferred embodiments, the porosity of the carrier material and/or the average pore size in the carrier material is such that the user is unable to draw a substantial quantity of air through the carrier material pores during inhalation.

Similarly, in particular embodiments, the pore size may be such that airflow within the pores of the carrier material is greatly reduced. The deliverable agent is released from the carrier material by evaporating it and allowing it to diffuse from the inner regions of the carrier material into the surrounding air. The surrounding air is drawn over the external surface of the carrier material whereupon it mixes with the vaporised deliverable agent and is carried to the user. The use of the term "external surface" in this context refers to the outermost surface of the solid material, e.g. the outer surface of the pellet, block or disc of carrier material. Such transport mechanisms are particularly important for carrier materials having small average pore sizes, such as not larger than about 100 µm (e.g. not larger than about 25 µm).

In a preferred embodiment, the carrier material has a porosity of from about 10% to about 90% (e.g. from about 10% to about 70%), and the average pore size in the carrier material is from about 0.1 µm to about 500 µm. In a further preferred embodiment, the carrier material has a porosity of from about 20% to about 70%, and the average pore size in the carrier material is from about 0.2 µm to about 200 µm.

In a further preferred embodiment, the carrier material has a high mechanical strength (e.g. compressive strength). In this respect, by material of "high mechanical strength" we also include that the structure of that carrier material pore network maintains its overall integrity (e.g. shape, size, porosity, etc.) when a force of about 1 kg-force/cm$^2$ (0.098 MPa), such as about 5 kg-force/cm$^2$ (0.49 MPa), such as about 7.5 kg-force/cm$^2$, e.g. about 10.0 kg-force/cm$^2$, preferably about 15 kg-force/cm$^2$, more preferably about 20 kg-force/cm$^2$, for example about 50 kg-force/cm$^2$, especially about 100 kg-force/cm$^2$ or even about 125 kg-force/cm$^2$ (12.25 MPa) is applied using routine mechanical strength testing techniques known to the skilled person (for example using a so-called "compression test" or "diametral compression test", employing a suitable instrument, such as that produced by Instron (the "Instron Test", in which a specimen is compressed, deformation at various loads is recorded, compressive stress and strain are calculated and plotted as a stress-strain diagram which is used to determine elastic limit, proportional limit, yield point, yield strength and (for some materials) compressive strength)). The mechanical strength is also typically not greater than about 2040 kg-force/cm$^2$ (200 MPa), as materials with a very high mechanical strength may have insufficient porosity to enable an adequate quantity of the deliverable agent to be incorporated therein. In embodiments, therefore, the mechanical strength is less than about 200 MPa, preferably less than about 100 MPa.

A particularly preferred carrier material is one in which the size and interconnectivity of the pores is such that the transmission of significant quantities of air through the pores of the carrier material cannot be achieved through inhalation by the user. By this, we mean that a healthy adult is incapable of inhaling an amount corresponding approximately to an average person's inspiratory capacity (e.g. about 3 litres) through the carrier material in a period of about 20 seconds. Such a carrier material would typically have a porosity of no more than 50%, and/or an average pore size not exceeding about 100 µm, though such materials could have higher porosities if the average pore size were smaller and vice versa. Thus in a particular embodiment, the carrier material has a porosity of up to 50% (e.g. from about 10% to about 50%), and an average pore size of up to about 100 µm (e.g. from about 0.1 µm to about 100 µm). In a further embodiment, the carrier material has a porosity of up to 50% (e.g. from about 10% to about 50%), and an average pore size of up to about 50 µm (e.g. from about 0.1 µm to about 50 µm). In all of the embodiments described herein, the pores are preferably interconnected to allow deliverable agent to be released from the inner regions of the carrier material (i.e. the regions that are located distally from the external surface of the carrier material). The carrier material should however have sufficient porosity, at least in the external regions, to enable a sufficient quantity (e.g. at least one therapeutic dose) of the deliverable agent to be contained in those pores prior to use.

In an embodiment of the invention, the deliverable agent is located predominantly within the pores of the carrier material. By the use of the phrase "predominantly within the pores of the carrier material" it is intended that at least 50% by weight of the deliverable agent in the device is located within the pores of the carrier material. In particular embodiments of the invention, at least 75% by weight (or, for a gas, at least 75% by volume) of the deliverable agent in the device is located within the pores of the carrier material. In preferred embodiments, at least 90% by weight (or at least 90% by volume) of the deliverable agent in the device is located within the pores of the carrier material. By locating the deliverable agent predominantly or essentially completely within the pores of the carrier material, greater control can be achieved over the amount of deliverable agent that is vaporised and delivered to the user during use. In a particular embodiment, the device does not comprise a separate reservoir of deliverable agent that is separate from the carrier material. That is, essentially all of the deliverable agent is located in association with the carrier material, or preferably essentially all of the deliverable agent is located within the pores of the carrier material.

By largely or completely containing the deliverable agent in the pores of the carrier material, this also reduces the possibility of deliberate ex vivo extraction of drug for intended abuse (e.g. by acid or alcohol extraction, followed by injection).

It is particularly preferred that the deliverable agent is located predominantly within the pores of the carrier material when the deliverable agent is one or more therapeutic agents (i.e. active pharmaceutical ingredients) that is open to abuse potential. This is advantageous as it hinders the release of the deliverable agent from the device, and thereby reduces the risk of the device containing the deliverable agent from being used as an illicit source of that deliverable agent.

It is also preferred that the carrier materials used in the devices of the invention are capable of storing and releasing a sufficient quantity of the deliverable agent during use such that it is not necessary for the device to contain an additional reservoir of the deliverable agent. That is, in preferred embodiments, the device does not contain a store of deliverable agent other than that which is associated with (i.e. predominantly located within the pores of) the carrier material prior to use.

Porous carrier materials typically contain both open pores and closed pores. The term "open pores" refers to pores (e.g. voids within the material) that are open to the external environment such that, when those pores are otherwise empty, gases in the environment are able to pass in and out of those pores. Such pores are generally located at or close to the surface of the individual carrier material particles. The term "closed pores" refers to pores which are located within particles of carrier material away from the external surfaces, and which may contain material (e.g. gases) which is not able to freely exchange with the external environment.

In an embodiment of the invention, pores of the porous carrier material are saturated with the deliverable agent. In devices in which the deliverable agent is present as part of a mixture containing one or more additional substances mentioned elsewhere herein (e.g. evaporation enhancing agents, flavouring agents, taste enhancers, etc.), then the pores of the porous carrier material are may be saturated with said mixture. In this context, the pores that are saturated with the deliverable agent (or mixture containing the deliverable agent) include at least the open pores. The closed pores present in the carrier material may or may not also contain the deliverable agent (or mixture containing the deliverable agent). It is not necessary for the closed pores to be saturated with the deliverable agent (or mixture containing the deliverable agent). By the use of the term "saturated" it is intended that the pores (e.g. at least the open pores) are predominantly filled (e.g. substantially completely filled) with the deliverable agent (or mixture containing the deliverable agent), and preferably that the pores contain essentially only the deliverable agent (or mixture containing the deliverable agent). These pores should contain a minimal quantity of vacant space (e.g. space that is occupied by atmospheric gases or materials other than the deliverable agent). For the avoidance of doubt, the devices of the present invention may contain a plurality of deliverable agents, and references herein to pores which contain essentially only the deliverable agent also refer to pores, which contain essentially only the plurality of deliverable agents.

In a preferred embodiment, at least about 70% of the cavity volume of the open pores of the porous carrier material is filled with the deliverable agent (or mixture containing the deliverable agent). In a further embodiment at least about 90% (e.g. at least about 95%) of the volume of the open pores of the porous carrier material is filled with the deliverable agent (or mixture containing the deliverable agent).

The devices of the present invention comprise a solid, porous carrier material having a porosity of at least 10%, wherein at least a portion of the deliverable agent is located within the pores of said carrier material. The device is further configured such that it is operable to heat the carrier material and thereby vaporise the deliverable agent. The carrier materials and deliverable agents described herein may be used in any conventional inhalation device which is configured to deliver one or more substances to a user in the form of an aerosol or vapour (i.e. gas). Such devices would be known to the skilled person and include electronic cigarettes known as "e-Cigs", for example as described in US 2014/0014126, and other inhalation devices, for example as described in U.S. Pat. No. 4,303,083.

Inhalation devices may also be constructed so that they are capable of being used only with the carrier materials and deliverable agents described herein. This may be achieved in a number of ways, e.g. by ensuring that replaceable cartridges (such as those described elsewhere herein) require a specific 3-dimensional shape in order for the carrier material to be heated by the device, or by incorporating conducting material (e.g. iron particles) within the carrier material for induction heating purposes. Additional methods will be known to the skilled person. Such devices are particularly useful as it would be very difficult for drug abusers to use those devices to abuse other drug products.

In an embodiment of the invention, the carrier material containing the substance to be inhaled (i.e. the deliverable agent) is located within the device in gaseous connection with an opening (e.g. a mouthpiece) located on an external surface of the device. When in use, deliverable agent within the carrier material is vaporised, whereupon the vapour flows to the opening and is received by the user (e.g. via a mouthpiece).

The movement of the vapour within the device is typically achieved by the user inhaling at the mouthpiece and thereby drawing the gases out of the inhalation device. The device may also contain a second opening which is in gaseous connection with both the carrier material containing the deliverable agent and the first opening (e.g. mouthpiece) mentioned hereinbefore. This configuration allows the user to draw air through the internal regions of the inhalation device and thereby facilitate the delivery to the user of the vaporised material following generation within the device.

In the devices of the present invention, the substance to be inhaled (i.e. the deliverable agent) is typically a solid, a liquid or a gas under ambient conditions. The inhalation device contains a supply of the substance to be inhaled (e.g. in a solid or liquid form, or as a dissolved or suspended gas), together with means by which said substance may be volatilised. Suitable means include any heat source which is capable of delivering thermal energy directly to the carrier material in order to vaporise the deliverable agent that is also present. The deliverable agent is thereby release in the form of an aerosol or a gas (i.e. a vapour). The vaporised material is then delivered to the user, typically by the user inhaling said vapours. Suitable heating apparatuses that may be used to heat the carrier material will be known to the skilled person.

In one embodiment, the carrier material may be directly heated by a flame. In such an embodiment, the device contains a supply of a flammable gas which is capable of being ignited to heat the carrier material.

In a preferred embodiment, the device comprises a heating element (e.g. an electric heating element) which is operable to heat the carrier material and thereby vaporise at least a portion of the deliverable agent that is located within the pores of the carrier material. For example, the heating element may be a resistance heater (e.g. in the form of a conducting wire or a heating plate) which releases an effective amount of heat when a current is passed through it. Heating may also occur by way of induction heating. This may be achieved by locating the carrier material in close proximity to a heating element (e.g. a metal object or other conducting structure) which, in turn, may be heated by induction using an electromagnet.

In a further embodiment, the heating element is located proximally to (i.e. in close proximity to, or preferably directly adjacent to) the carrier material. By this, it is meant that the heating element is positioned sufficiently close to the carrier material to allow the heating element to directly heat the carrier material and vaporise the deliverable agent. The heating element may be in direct contact with the carrier material, and furthermore may be intimately mixed into the carrier material. An example of such a heating element is one in which the heating element is a heating coil. Said coil may be wrapped around the outer wall of a block or pellet of carrier material, or it may be embedded within the carrier material mass. Embedding is typically achieved by incorporating the heating element into the mixture of carrier material precursor substances prior to curing or hardening of that mixture, as is described elsewhere herein. The carrier materials used in the devices of the present invention are capable of being heated directly (i.e. rather than via a flow of hot gas originating from the heating element) without degrading and without producing an unpleasant taste for the user. In another embodiment, the heating element is not mixed into the carrier material, but is located adjacent to or distally from the carrier material. In such embodiments, the heating element may be used to heat air which can then be made to flow over and/or through the carrier material containing the deliverable agent in order to vaporise at least a portion of the deliverable agent that is located within the pores of the carrier material.

Systems in which induction heating is used to heat the carrier material and deliverable agent typically require a metal object or other electrically conducting structure to be present as the heating element in close association with the carrier material and deliverable agent. Discrete particles (e.g. spheres or granules) of a suitable conducting material (e.g. iron or copper) may be dispersed throughout the carrier material to aid in the heating process. The use of such systems allows the device to rapidly end evenly heat the whole volume of carrier material very quickly, and thereby ensure that the amount of deliverable agent that is release is better controlled and more predictable. The suitable conducting material may also be provided in other suitable shapes and geometries, for example, it may be provided as a series of rods, discs or plates, or as a mesh or 3-dimensional network within which the carrier material and deliverable agent may be located. Where the conducting material is dispersed throughout the carrier (e.g. as small particles, rods or a mesh), then typically the amount of conducting material present should be sufficient to ensure that the carrier material can be heated rapidly and thoroughly throughout, and the amount should be low enough to avoid interfering with the efficacy of the ceramic carrier and its contents. Typically, the amount of conducting material (i.e. the heating element) present in the carrier material may be as high as 40% by weight relative to the total weight of the conducting material and carrier material without significantly reducing the mechanical properties of the hardened cement. Preferably, the amount of conducting material present in the carrier material will be no more than 20% by weight relative to the total weight of the conducting material and carrier material. Where the carrier material is formed in contact with only a small number (e.g. less than five, preferably one) larger conducting masses, then the relative amount of conducting material present as the heating element may be much higher, potentially up to 70% (e.g. up to 50%) by weight relative to the total weight of the conducting material and carrier material. In this respect, 3-dimensional networks may be obtained by any conventional method known to the skilled person including 3D printing or foamed metal formation as described elsewhere herein.

The conducting material may also comprise or consist of a ferromagnetic (or ferrimagnetic) material, such as iron. The presence of such magnetic materials can further enhance the heating effects achieved using induction heating because additional heat is generated through magnetic hysteresis losses within the magnetic material. Induction heating is generally able to provide faster heating of materials compared to resistance heaters.

Conducting material (e.g. in the form of particles) may also be mixed with the carrier material even in systems which are not intended for induction heating. Irrespective of the method by which the carrier material is heated, the conducting material helps to increase the speed and homogeneity of heat conduction throughout the carrier material to thereby improve the speed and predictability of the evaporation of the deliverable agent.

The carrier material may be housed within an outer casing located within the inhalation device. For example, the carrier material may be housed within a casing which is formed from a thermally conductive material (e.g. a metal such as aluminium or steel) that is capable of storing the carrier material and the deliverable agent when the device is not in use. In such an embodiment, the heating element may also be in direct thermal contact with the external surface of the casing.

Alternatively, the casing may be a ceramic or geopolymeric material, e.g. as defined hereinafter. Preferably, the casing is a ceramic material (either the same as or different from the ceramic carrier described herein) which does not contain any deliverable agent within its pores. Such a ceramic casing provides thermal insulation to the carrier material and deliverable agent contained within it. Ceramic casings are particularly useful in devices of the invention in which carrier materials are heated using induction heating. In these systems, the casing may act as a store for the carrier material containing the heating element (e.g. particles of conducting material) and separate it from the source of alternating magnetic field (e.g. a conducting coil) and from other components of the inhalation device that may be sensitive to high temperatures.

In a further embodiment, a portion of the heating element may be located internally to the carrier material. For example, some or all of the heating element may be at least partially surrounded by the carrier material. In such devices, the carrier material is shaped complementally with the shape of the heating element; that is, the shape of the carrier material fits with the shape of the heating element in order to facilitate a close association between the heating element and the carrier material. This ensures that there is a relatively high area of association between the heating element and the carrier material. The construction of the device in this way allows for a more rapid and efficient heat transfer from the heating element to the carrier material to further aid in controlling of the release of the deliverable agent. "Control of release" may refer to control of the total amount and/or the rate of release of the deliverable agent from the device when in use.

The carrier material may be manufactured in situ, i.e. in the presence of the heating element, in order to ensure that the carrier material is shaped complementally with the shape of the heating element. The formation of the carrier material in this way may be achieved in cases where the carrier material is formed from a paste. Said paste is applied to the heating element (which may, for example, be shaped in a coil, grid or straight wire) and then allowed to harden. Alternatively, the carrier material may be provided as a solid which is pre-formed so as to fit with a particular heating element design. For example, the carrier material may be provided as a block of material which optionally contains one or more cavities (e.g. cylindrical bore) into which a heating element may be located once the inhalation device has been assembled. Alternatively, the carrier material may be formed from a paste which is applied to a mould, allowed to harden and then removed from the mould so that it can be incorporated into an inhalation device at a later date. The mould is shaped so that the carrier material solidifies in a form (i.e. shape) that complements the particular heating element design. In embodiments in which the carrier material is provided as a component in a replaceable cartridge (as hereinafter described), pre-formed units of carrier material having a standardised shape may be used in those cartridges. Carrier materials which may be formed at relatively low temperatures (e.g. below 400° C.), such as chemically bonded ceramics and geopolymers, are particularly suited for the manufacture of pre-formed units due to the mouldable properties of the unhardened carrier material mixtures.

Carrier materials which may be formed at relatively low temperatures (e.g. below 400° C.), such as chemically bonded ceramics and geopolymers, are also particularly suited for use with induction heating systems. The conducting material (whether it is in the form of discrete particles or any other structure(s)) may be interspersed throughout the mixture of the carrier material and deliverable agent by introducing the conducting material before the carrier material is hardened or cured. The composite mixture comprising the carrier material (or its precursors), the deliverable agent and the conducting material is typically a paste which can be moulded into any desired shape after the conducting material has been added. The composite can then be hardened without the use of high temperatures which might melt the conducting material. Conversely, conventional sintering processes can involve temperatures which are in excess of 1000° C. and which may melt many metals.

The conducting material may alternatively be a 3D network of metal, which is obtainable by methods including 3D printing. The composite mixture comprising the carrier material (or its precursors), the deliverable agent and the conducting material can be obtained by first preparing the 3D network of metal and then incorporating a mouldable ceramic carrier precursor paste which contains both the ceramic carrier precursor(s) and the deliverable agent.

In certain embodiments, the device is refillable. In one example, following use, i.e. when the store of deliverable agent in the device is partially or completely depleted, a further supply of the deliverable agent may be incorporated into the pores of the carrier material in order to replenish the device. This may be achieved by bringing the fully or partly exhausted carrier material into fluid contact with an external reservoir containing the deliverable agent for a defined period of time. Such an external reservoir is preferably provided as a stock of deliverable agent (or a material comprising the deliverable agent) which is stored separately from the device between each refilling.

The carrier material and the deliverable agent may alternatively be provided together in a replaceable cartridge. Such a cartridge should be suitable for use in the inhalation devices of the invention as described herein. In such a system, the store of deliverable agent in the device may be easily replenished by removing a spent cartridge from the inhalation device and replacing it with a full cartridge (i.e. a cartridge which contains the desired quantity of deliverable agent). Inhalation devices which allow for the replacement of cartridges containing deliverable agent are also refillable devices.

Thus according to a second aspect of the invention, there is provided a cartridge suitable for use in an inhalation device as described herein, wherein the cartridge contains:

(i) a solid, porous carrier material having a porosity of at least 10%; and (ii) a deliverable agent as hereinbefore defined located within the pores of the carrier material.

As the devices of the invention are intended for use in the delivery of active pharmaceutical ingredients, individual formulation units (e.g. in the form of replaceable cartridges as described above, or in the form of blocks, pellets, tablets, discs or sticks as described below) that contain one or more active pharmaceutical ingredients and that are suitable for use with these devices may be provided to the end-user. These individual formulations units therefore represent an embodiment of the "cartridge" that is the second aspect of the invention.

The individual formulation units themselves may be supplied to the end-user separately from, or together with, the inhalation device. Each individual formulation unit contains a sufficient amount of the active pharmaceutical ingredient to provide the desired number of doses (e.g. not more than one or two doses for abusable substances such as opioid analgesics) to the user, and so may be described as a "unit dose formulation" or a "controlled dose formulation". When a patient is prescribed a treatment regime involving multiple doses of a drug, that drug (preferably a non-abusable drug) may be supplied in a controlled dose formulation in which each unit (i.e. each pellet, tablet, etc.) contains a sufficient amount of drug to provide a plurality of doses (e.g. at least 5, at least 20, or at least 100 doses) when used in the device of the invention. For controlled dose formulations which contain a plurality of doses, those formulations may be heated in the devices multiple times throughout the course of treatment with each heating event facilitating the delivery of separate dose to the patient.

In a further embodiment, there is provided a unit product (e.g. a replaceable cartridge, a unit dose formulation or a controlled dose formulation) containing:

(i) a solid, porous carrier material having a porosity of at least 10%;

(ii) a deliverable agent as hereinbefore defined located within the pores of the carrier material; and (iii) particles of a conducting material (e.g. a metal) distributed throughout the carrier material.

In such an embodiment, the unit product may be used as a replacement for a spent cartridge in an inhalation device as described herein. The carrier material, deliverable agent and conducting material may each be as described elsewhere herein. Such unit products may each contain a defined quantity of the deliverable agent, for example a sufficient amount of the deliverable agent to allow a controlled dose (e.g. no more than about one unit dose) to be delivered to the recipient via inhalation before that unit product is effectively exhausted.

In embodiments in which the carrier material and the deliverable agent are provided together in a replaceable cartridge, unit dose formulation, controlled dose formulation, or the like, the cartridge or formulation may be constructed so that it can be easily removed from the device by the user in order for a replacement cartridge or formulation (e.g. a replenished cartridge or formulation) to be introduced in its place.

In one embodiment, the replacement cartridge, unit dose formulation, controlled dose formulation, or the like may be configured such that the carrier and the deliverable agent are positioned in close proximity to a heating element in the device following insertion of the cartridge, while being simultaneously configured such that the user in unable to come into physical contact with the deliverable agent at any time prior to activation of the device. This may help to reduce the risk of unintended exposure of the user to the deliverable agent when replenishing the device. Alternatively, or additionally, the replacement cartridge, unit dose formulation, controlled dose formulation, or the like may contain a composite carrier material, i.e. a material which comprises a carrier material (e.g. a chemically bonded ceramic or geopolymeric material), a deliverable agent and particles of a conducting material.

The replacement cartridges may contain the carrier material and the deliverable agent together within a casing as hereinbefore described (e.g. a shell made of a different material from the carrier material, preferably a metal, an alloy, a ceramic or a geopolymer) so as to reduce the exposure of the user to the deliverable agent, or to minimise unintended loss of the deliverable agent during storage or insertion into the device.

In an alternative embodiment, the cartridge or formulation may consist essentially of the carrier material and the deliverable agent, optionally together with particles of a conducting material and/or one or more additional substances mentioned elsewhere herein that may be present (e.g. evaporation enhancing agents, flavouring agents, taste enhancers, fillers, etc., as would be known to the skilled person). For example, the cartridge may not contain any other elements (aside from the carrier material and the deliverable agent) that are required for the functioning of the device.

Embodiments in which the cartridge or formulation consists essentially of the carrier material and the deliverable agent (optionally together with particles of a conducting material and/or one or more additional substances mentioned elsewhere herein) may particularly be mentioned in the context of the delivery of active pharmaceutical ingredient. Such cartridges or formulations may be conveniently provided to a doctor, pharmacist or patient in the form of single-dose or multi-dose formulation units wherein each unit contains a defined quantity of the active pharmaceutical ingredient. By supplying formulations to end-users in the form of single-dose units, drug-abusers are further hindered from obtaining large quantities of abusable drug from such formulations.

The inhalation device may be configured such that, after use, the user simply needs to remove the spent carrier material from the device and insert a replacement unit of carrier material containing a full supply of the deliverable agent (e.g. drug). Such replacement units could be provided as blocks, discs, tablets, sticks or pellets of carrier material containing the deliverable agent. Such replacement units could be provided in the commonly used packaging commercially known as a "blister pack" with each unit vacuum packaged, sealed and individually removable for insertion into the device. The provision of such replacement units would minimise wastage and ensure that spare cartridges would be small and could be conveniently stored by the user.

The use of a cartridge system may allow for greater control of the quantity of deliverable agent that is delivered to the user. For example, each cartridge may contain a sufficient quantity of the deliverable agent (e.g. an active pharmaceutical ingredient) to provide a defined amount (e.g. no more than one pharmaceutical dosage) of that deliverable agent to the user.

In embodiments in which the inhalation devices are intended to be used to deliver one or more active pharmaceutical ingredients, each individual device may contain a sufficient quantity of the (or each) active pharmaceutical ingredient to provide a limited but defined amount of the active pharmaceutical ingredient to the user. In a preferred embodiment, said amount may be a single (i.e. no more than one) therapeutic dosage. In such embodiments, the device is incapable of delivering additional quantities of the active pharmaceutical ingredient once the above-mentioned limited amount has been depleted. Such devices may be refillable (e.g. via the cartridge system as hereinbefore defined) or they may be intended for only a limited number of uses after which they must be disposed of.

Advantageously, the inhalation devices of the invention may contain more than one carrier material, or a carrier material in which different regions have different average pore sizes. This enables the inhalation devices to be configured so as to release the one or more deliverable agents at a plurality of rates. For example, such a device may be able to provide an initial rapid release of a controlled amount of drug followed by a slower sustained release of a controlled amount of either the same or a different drug, depending on the needs of the user.

In a preferred embodiment, the carrier material is based on one or more ceramic materials, one or more geopolymeric materials or one or more metals. It is particularly preferred that the carrier material is based on one or more chemically bonded ceramic materials or one or more geopolymeric materials.

For example, the carrier material may be based on one or more sintered ceramic materials.

The term "ceramic" will be understood to include compounds formed between metallic and nonmetallic elements, frequently oxides, nitrides and carbides that are formed and/or processable by some form of curing process, which often includes the action of heat. In this respect, clay materials, cement and glasses are included within the definition of ceramics (Callister, "*Material Science and Engineering, An Introduction*" John Wiley & Sons, 7$^{th}$ edition (2007)).

Ceramics may comprise sintered ceramics (for example kaolin, metakaolin, aluminium oxide, silicon nitride, zirconium oxide, silicon carbide, or a mixture thereof).

It is preferred that the ceramic material that is employed is based upon a metal oxide (such as aluminum oxide or zirconium oxide), or ceramics based on oxides of metals (or metalloids or non-metals) are particularly useful as they are incapable of undergoing further oxidation and so exhibit good stability at high temperatures.

The ceramic material may also be an oxide and/or a double oxide, and/or a nitride and/or a carbide of any of the elements scandium, cerium, yttrium, boron, or, preferably, silicon, aluminium, carbon, titanium, zirconium or tantalum, or combinations thereof.

In a preferred embodiment, the ceramic material is an oxide, a nitride and/or a carbide of any of the elements silicon, aluminium, carbon, titanium, zirconium or tantalum, or combinations thereof. Particular materials that may be mentioned include aluminium oxide, zirconia, silicon carbide, silicon nitride, and combinations thereof.

Sintered ceramics (including materials that are formed from aluminium oxide, zirconium oxide, silicon carbide and/or silicon nitride) are well known to the skilled person. Such sintered ceramics are particularly useful as carrier materials in inhalation devices in which the deliverable agent is a therapeutic agent that is not open to abuse by the recipient.

Sintered ceramics may be loaded with the deliverable agent after the sintering has taken place and the ceramic has been formed. Loading is typically achieved by soaking the carrier material in a liquid containing the deliverable agent. The loading efficacy associated with soaking may be improved using vacuum loading techniques. Other methods which facilitate the drawing up of the deliverable agent into the pores of the carrier material via capillary forces may also be used. For example, the deliverable agent may be applied to the ceramic by spraying, brushing, rolling, dip coating, powder coating, misting.

Pore sizes in the carrier material may be controlled by various techniques known to the skilled person. For ceramics (and geopolymers), control of size of pores is typically achieved during the process of fabricating the carrier material network structure. Examples of methods that are known for the fabrication of porous scaffolds are disclosed in Subia B. et al. (2010) *Biomaterial Scaffold Fabrication Techniques for Potential Tissue Engineering Applications*, Tissue Engineering, Daniel Eberli (Ed.).

A particular method that is suitable for use with the ceramic carrier materials used in the present invention is the porogen leaching method which involves the use of a sacrificial phase during the formation of the carrier material. A porogenic material may be included as part of the reaction mixture during the formation of the carrier material in order to assist in the formation of pores within the final carrier material network. Porogenic materials include, for example, oils, liquids (e.g. water), sugars, mannitol etc. The porogenic material may then be removed from the carrier material, e.g. by burning it away when the carrier material is heated during the curing or sintering process, or by dissolving it away using an appropriate solvent, e.g. water.

In ceramic materials which are typically produced via a sintering process, the final porosity may also be controlled by ensuring that the sintering process is only partially completed. Sintering is broadly defined as the consolidation upon heating of a loose mass of particles, which are in contact with each other, to a denser mass. It results in a decrease of specific surface area and porosity and in an increase of density. Generally, sintering occurs in three stages. During the initial stage, contact areas between the individual particles are formed through contact sintering and densification sintering. In the intermediate stage, contact regions between neighbouring particles grow and the large number of small particles are replaced by a smaller number of large grains. Intensive shrinkage of open pores occurs between the grain boundaries, and this is associated with a change in pore geometry. In the final stage of sintering, grain boundary and lattice diffusion are the dominant mass transport mechanisms. Isolated closed pores are formed which shrink in size as densification proceeds.

In order to achieve the desired level of porosity, the precursor for a sintered ceramic may be heated to a lower temperature, under a lower pressure, or for a shorter time than is typically the case during the normal sintering process, thereby allowing pores of a much larger size to be retained. Another method for controlling the porosity of the final product involves providing a green body (i.e. the material which is to be sintered) having a particular initial porosity. A further method involves the addition of a controlled quantity of a sacrificial material which is lost during the sintering process. Suitable methods for controlling the porosity of sintered ceramics are disclosed in Journal of the European Ceramic Society, Vol. 29, No. 13, 2009, 2867-2872.

Alternatively, the carrier material may be based on one or more chemically bonded ceramic materials. One or both of these may be provided in the form of granules.

Suitable chemically bonded ceramics include non-hydrated, partly hydrated or fully hydrated ceramics, or combinations thereof.

Non-limiting examples of chemically bonded ceramic systems include calcium phosphates, calcium sulphates, calcium carbonates, calcium silicates, calcium aluminates, magnesium carbonates and combinations thereof. Preferred chemical compositions include those based on chemically bonded ceramics, which following hydration of one or more appropriate precursor substances consume a controlled amount of water to form a network.

Other particular systems available are those based on aluminates and silicates, both of which consume a great amount of water. Phases such CA2, CA, CA3 and C12A7, and C2S and C3S in crystalline or amorphous state (C=CaO, A=$Al_2O_3$, $SiO_2$=S, according to common cement terminology) may be used, which are readily available. The calcium aluminate and/or calcium silicate phases may be used as separate phase or as mixtures of phases. The above-mentioned phases, all in non-hydrated form, act as the binder phase (the cement) in the carrier material when hydrated. The liquid(water)-to-cement weight ratio is typically in the region of 0.2 to 0.5, preferably in the region of 0.3 to 0.4.

Further materials that may be mentioned in this respect include clay minerals such as aluminium silicate and/or aluminium silicate hydrate (crystalline or amorphous). Non-limiting examples include kaolin, dickite, halloysite, nacrite, ceolite, illite or combinations thereof, preferably halloysite.

In further embodiments of the invention, the porous solid is based on a ceramic material that is formed from a self-setting ceramic. Non-limiting examples of self-setting ceramics include calcium sulphate, calcium phosphate, calcium silicate and calcium aluminate based materials. Particular ceramics that may be mentioned in this respect include alpha-tricalcium phosphate, calcium sulphate hemihydrate, $CaOAl_2O_3$, $CaO(SiO_2)_3$, $CaO(SiO_2)_2$, and the like.

Other ceramic materials that may be employed include those based upon a sulphate, such as a calcium sulphate or a phosphate such as a calcium phosphate. Particular examples of such substances include alpha or beta phase calcium sulphate hemihydrate (end product calcium sulphate dihydrate), alkaline or neutral calcium phosphate (apatite) and acidic calcium phosphate (brushite). As with sintered ceramics, chemically bonded ceramics may be loaded by soaking the ceramic material in a liquid containing the deliverable agent, or through any other method which facilitates the drawing up of the deliverable agent into the pores of the ceramic material via capillary forces (including spraying, brushing, rolling, dip coating, powder coating or misting).

The grain size of the ceramic material (e.g. aluminium silicate) may be below about 500 μm, preferably below about 100 μm, more preferably below about 50 μm, and particularly below about 20 μm, as measured by laser diffraction in the volume average mode (e.g. Malvern master size). The use of ceramic material with larger grain sizes may result in a less optimal setting and reduction in the strength of the final solid, though may allow for a better handling of the cement. The grains may be of any shape (e.g. spherical, rounded, needle, plates, etc.). Carrier materials with grain sizes below 1 μm may be used in the devices of the invention, but preferred grain sizes are at least 1 μm, in order to aid with manufacturing (to avoid forming very viscous pastes when wetted), and preferably in the region of about 10 μm. These grain sizes are appropriate for all ceramics in the context of the devices of the invention, including but not limited to both the sintered and chemically bonded ceramics described herein. The grains may be of any shape (e.g. spherical, rounded, needle, plates, etc.). For the avoidance of doubt, where the carrier material is formed from geopolymers, the grain size of the material may similarly be below about 100 μm, more preferably below about 50 μm, and particularly below about 20 μm.

The mean grain size of any ceramic precursor powder particles may be below about 500 μm, e.g. below about 100 μm, preferably between about 1 μm and about 30 μm. This is to enhance hydration. Such precursor material may be transformed into a nano-size microstructure during hydration. This reaction involves dissolution of the precursor material and repeated subsequent precipitation of nano-size hydrates in the water (solution) and upon remaining non-hydrated precursor material. This reaction favourably continues until precursor materials have been transformed and/or until a pre-selected porosity determined by partial hydration using the time and temperature, as well as the $H_2O$ in liquid and/or humidity, is measured.

Chemically bonded ceramics are particularly suitable for use as carrier materials for active pharmaceutical ingredients. These carrier materials are relatively cheap and easy to manufacture and provide adequate release of the volatile deliverable agent upon the application of heat.

For the avoidance of doubt, the porous solid material may comprise more than one ceramic material, e.g. including a mixture of sintered and chemically bonded ceramics.

Pore sizes in chemically bonded ceramics may be controlled by various techniques during the process of fabricating the carrier material network structure. A particular method that is suitable for use with the chemically bonded ceramic carrier materials used in the present invention is the porogen leaching method which involves the use of a sacrificial phase during the formation of the carrier material. A porogenic material may be included as part of the reaction mixture during the formation of the carrier material in order to assist in the formation of pores within the final carrier material network. Porogenic materials include, for example, oils, liquids (e.g. water), sugars, mannitol etc. The porogenic material may then be removed from the carrier material, e.g. by burning it away when the carrier material is heated during the curing process, or by dissolving it away using an appropriate solvent. Dissolving is usually achieved with water in order to avoid leaving residual amounts of a substance which may have deleterious effects on the working of the device or adverse effects on the user.

Foaming methods may also be used to increase the pore sizes in chemically bonded ceramics, as well as other carrier materials mentioned herein. Such methods would be known to the skilled person and are particularly useful for forming carrier materials with larger pore sizes.

Alternatively, the carrier material may be based on one or more geopolymer materials.

The term "geopolymer" will be understood by those skilled in the art to include or mean any material selected from the class of synthetic or natural aluminosilicate materials which may be formed by reaction of an aluminosilicate precursor material (preferably in the form of a powder) with an aqueous alkaline liquid (e.g. solution), preferably in the presence of a source of silica.

The term "source of silica" will be understood to include any form of a silicon oxide, such as $SiO_2$, including a silicate. The skilled person with appreciate that silica may be manufactured in several forms, including glass, crystal, gel, aerogel, fumed silica (or pyrogenic silica) and colloidal silica (e.g. Aerosil).

Suitable aluminosilicate precursor materials are typically (but not necessarily) crystalline in their nature and include kaolin, dickite, halloysite, nacrite, zeolites, illite, preferably dehydroxylated zeolite, halloysite or kaolin and, more preferably, metakaolin (i.e. dehydroxylated kaolin). Dehydroxylation (of e.g. kaolin) is preferably performed by calcining (i.e. heating) of hydroxylated aluminosilicate at temperatures above 400° C. For example, metakaolin may be prepared as described by Stevenson and Sagoe-Crentsil in *J. Mater. Sci.*, 40, 2023 (2005) and Zoulgami et al in *Eur. Phys J. AP,* 19, 173 (2002), and/or as described hereinafter. Dehydroxylated aluminosilicate may also be manufactured by condensation of a source of silica and a vapour comprising a source of alumina (e.g. $Al_2O_3$).

Thus in a further embodiment, the carrier material may be a material obtainable by the process of reacting an aluminosilicate precursor material, such as a material selected from the group consisting of kaolin, dickite, halloysite, nacrite, zeolites, illite, dehydroxylated zeolite, dehydroxylated halloysite and metakaolin, with an aqueous alkaline liquid, optionally in the presence of a source of silica.

Precursor substances may also be manufactured using sol-gel methods, typically leading to nanometer sized amorphous powder (or partly crystalline) precursors of aluminosilicate, as described in Zheng et al in *J. Materials Science,* 44, 3991-3996 (2009). This results in a finer microstructure of the hardened material. (Such as sol-gel route may also be used in the manufacture of precursor substances for the chemically bonded ceramic materials hereinbefore described.)

If provided in the form of a powder, the mean grain size of the aluminosilicate precursor particles are below about 500 μm, preferably below about 100 μm, more preferred below about 30 μm.

In the formation of geopolymer materials, such precursor substances may be dissolved in an aqueous alkaline solution, for example with a pH value of at least about 12, such as at least about 13. Suitable sources of hydroxide ions include strong inorganic bases, such as alkali or alkaline earth metal (e.g. Ba, Mg or, more preferably, Ca or, especially Na or K, or combinations thereof) hydroxides (e.g. sodium hydroxide). The molar ratio of metal cation to water can vary between about 1:100 and about 10:1, preferably between about 1:20 and about 1:2.

A source of silica (e.g. a silicate, such as $SiO_2$) is preferably added to the reaction mixture by some means. For example, the aqueous alkaline liquid may comprise $SiO_2$, forming what is often referred to as waterglass, i.e. a sodium silicate solution. In such instances, the amount of $SiO_2$ to water in the liquid is preferably up to about 2:1, more preferably up to about 1:1, and most preferably up to about 1:2. The aqueous liquid may also optionally contain sodium aluminate.

Silicate (and/or alumina) may alternatively be added to the optionally powdered aluminosilicate precursor, preferably as fume silica (microsilica; AEROSIL® silica). The amount that may be added is preferably up to about 30 wt %, more preferably up to about 5 wt % of the aluminosilicate precursor.

The presence of free hydroxide ions in this intermediate alkaline mixture, causes aluminium and silicon atoms from the source material(s) to be dissolved. The geopolymer materials may then be formed by allowing the resultant mixture to set (cure or harden), during which process the aluminium and silicon atoms from the source materials reorientate to form a hard (and at least largely) amorphous geopolymeric material. Curing may be performed at room temperature, at elevated temperature or at reduced temperature, for example at around or just above ambient temperature (e.g. between about 20° C. and about 90° C., such as around 40° C.). The hardening may also be performed in any atmosphere, humidity or pressure (e.g. under vacuum or otherwise). The resultant inorganic polymer network is in general a highly-coordinated 3-dimensional aluminosilicate gel, with the negative charges on tetrahedral $Al^{3+}$ sites charge-balanced by alkali metal cations.

In this respect, a geopolymer-based carrier material may be formed by mixing a powder comprising the aluminosilicate precursor and an aqueous liquid (e.g. solution) comprising water, a source of hydroxide ions as described hereinbefore and the source of silica (e.g. silicate), to form a paste. The ratio of the liquid to the powder is preferably between about 0.2 and about 20 (w/w), more preferably between about 0.3 and about 10 (w/w). Calcium silicate and calcium aluminate may also be added to the aluminosilicate precursor component.

In a preferred embodiment of the invention, the deliverable agent is co-formedly interspersed in pores within the carrier material network. This means that, whatever process is employed to form the carrier material, it must also necessarily form pores within which the deliverable agent is interspersed. Carrier material which is based on one or more chemically bonded ceramic materials or one or more geopolymeric materials is particularly suited for use in such embodiments as the process by which the carrier material and its pore network is formed does not require very high temperatures, in contrast to sintered ceramics.

The deliverable agent (or a mixture containing the deliverable agent) may thus be mixed with the carrier material (e.g. the ceramic, geopolymer or metal) or precursor(s) thereto, by way of a variety of techniques, such as introduction by way of a sol-gel process, as a solution, or as a slurry, a paste or a putty of, for example, particles, granules or pellets of carrier material or precursor(s) thereto, in the presence of an appropriate liquid (e.g. an aqueous or organic solvent). This is followed by some sort of "curing" process to form the sustained release composition, which comprises said pores, within which the deliverable agent resides. Carrier materials that are formed in this way may be said to be pre-loaded with the deliverable agent.

Such pores are themselves a three-dimensional network of channels or voids within the solid network, containing (e.g. particles of) the deliverable agent.

Such pores may thus be essentially "secondary pores" formed by chemical interactions (e.g. "bonding") between the surfaces of primary particles of carrier material (which may be porous in their own right (i.e. comprise "primary" pores), such as ceramics or geopolymers. Such pores may, for example, result from exposure of such materials to one or more chemical reagents that cause a physical and/or chemical transformation (such as a partial dissolution) at, and subsequent physical and/or chemical bonding together of, those surfaces (which may in itself result as a consequence of some other physico-chemical process such as drying, curing, etc.), giving rise to said pores/voids.

In such instances, such chemical reagents may be mixed together with the deliverable agent (or mixture containing the deliverable agent) during preparation of the carrier material. However, such secondary pores are not necessarily formed in this way, and bonding together of primary particles of carrier materials may also be physical and/or mechanical, or may be formed during the production of a three-dimensional, chemically bonded ceramic network as described hereinbefore, in the presence of the deliverable agent.

Thus, a device for delivering a deliverable agent in the form of an aerosol or vapour to a user is provided, comprising a carrier material which is a solid, continuous three-dimensional network comprising particles of a ceramic material, which particles are bonded together to form secondary pores or voids, and a deliverable agent present within said secondary pores or voids.

Alternatively, if the network is formed by way of a chemical reaction (e.g. polymerisation, or as described hereinbefore for geopolymers), deliverable agent may be co-mixed with a precursor mixture comprising relevant reactants and thereafter located within pores or voids that are formed during formation of the three-dimensional carrier material network itself.

It is particularly preferred that the ceramic material is one that is based on a chemically bonded ceramic or a geopolymer, as these materials are particularly suited for facilitating loading of the drug before the pore network is formed in the carrier. This, in turn, offers an effective method for readily controlling the amount of deliverable agent that is loaded into the carrier during manufacture. Such devices, most particularly those based on geopolymers, are advantageous when the inhalation device contains an active pharmaceutical ingredient that is open to abuse potential.

For geopolymers, control of size of pores is typically achieved during the process of fabricating the carrier material network structure. Examples of methods that are known for the fabrication of porous scaffolds are disclosed in Subia B. et al. (2010) *Biomaterial Scaffold Fabrication Techniques for Potential Tissue Engineering Applications*, Tissue Engineering, Daniel Eberli (Ed.).

A particular method that is suitable for use with the geopolymeric carrier materials used in the present invention is the porogen leaching method described above in respect of the ceramic carrier materials. Porogenic materials that may be used in the formation of porous geopolymeric material include, for example, oils, liquids (e.g. water), sugars, mannitol etc.

In a further alternative, the carrier material may be based on one or more metals.

By the use of the term "metal", we include both pure metals and alloys (i.e. mixtures or two or more metals). Suitable metals that may be used as carrier materials include those which remain solid up to and above the heating temperature used in the devices of the invention, e.g. above 400° C., or preferably above 500° C. Particular metal carrier materials include those based on titanium, nickel, chromium, copper, iron, aluminium, zinc, manganese, molybdenum, platinum and alloys containing those metals. So-called refractory metals may also be used in view of their high resistance to heat and wear.

Specific pure metals and alloys that may be used in this context include brass, manganese, molybdenum, nickel, platinum, zinc, and particularly include titanium, titanium alloys, nickel-chrome alloys, copper-nickel alloys, iron, steel (e.g. stainless steel), aluminium, iron-chromium-aluminium alloys.

Pore sizes in metallic carrier materials may be controlled by various techniques known to the skilled person. Examples of suitable methods that may be used to form a metallic substrate having the required porosity include three-dimensional printing and drilling. 3D printing of porous solids may be achieved using routine 3D printing apparatus, and pore sizes of as low as 10 µm can be achieved using this fabrication technique. Drilling methods for introducing porosity or increasing levels of porosity in materials are known to the skilled person. Such methods may be particularly advantageous as they provide a greater degree of control over pore sizes and the overall level of porosity in the material. Such drilling methods may be used to form pores having an average size as low as around 100 µm, and potentially lower.

Internal porosity can also be developed in metal structures (particularly where the metal structure is present as the conducting part of an induction heating system) by a gas expansion (or foaming) process based on hot isostatic pressing (HIPing). Porous bodies with typically 20-40% of isolated porosity are obtained by these processes. Porosity can be evolved much more rapidly when foaming occurs in highly reactive multi-component powder systems such as those which undergo self-propagating high temperature synthesis (SHS). The highly exothermic reactions, initiated either by local or global heating of compacted powder mixtures to the reaction ignition temperature, lead to vaporisation of hydrated oxides on the powder surfaces and the release of gases dissolved in the powder. The reacting powder mixture heats up rapidly to form a liquid containing (mostly hydrogen) gas bubbles and when the reaction is complete, cools rapidly, entrapping the gas to form a foam. Gas formation and foam expansion can be augmented by the addition of vapour forming phases such as carbon (which burns in air to produce CO) or foaming agents which react together to increase the reaction temperature and produce fine particles that stabilise the foam. Other suitable methods known to the skilled person are disclosed in Andrew Kennedy (2012). Porous Metals and Metal Foams Made from Powders, Powder Metallurgy, Dr. Katsuyoshi Kondoh (Ed.).

Any of the carrier materials described herein may be used in the devices of the invention. Thus, in a further embodiment, the invention relates to a device as hereinbefore described in which the ceramic material is selected from the list consisting of:

(i) an oxide, a nitride and/or a carbide of any of the elements silicon, aluminium, carbon, titanium, zirconium or tantalum, and combinations thereof;

(ii) a material obtainable by the process of reacting an aluminosilicate precursor material with an aqueous alkaline liquid;

(iii) a calcium phosphate, a calcium sulphate, a calcium carbonate, a calcium silicate, a calcium aluminate, a magnesium carbonate, an aluminium silicate, and combinations thereof; and (iv) brass, manganese, molybdenum, nickel, platinum, zinc, titanium, titanium alloys, nickel-chrome alloys, copper-nickel alloys, iron, steel, aluminium and iron-chromium-aluminium alloys.

The materials listed in (ii) and (iii) above are particularly preferred.

We have advantageously found that devices of the invention provide for release of the deliverable agent in the form of an aerosol or a vapour such that the deliverable agent can be administered to a user via inhalation. When in use, the inhalation device allows a deliverable agent to be inhaled by the user, typically for therapeutic purposes. In embodiments in which the deliverable agent is nicotine, the inhalation device may be used for therapeutic purposes, e.g. to reduce the frequency of smoking.

The deliverable agent may be provided in the device as part of a mixture comprising one or more additional components. One or more of said additional components may be present to facilitate the volatilisation of the deliverable agent when the carrier material is heated. In the inhalation devices of the present invention, the carrier material has a defined porosity, and this aids in controlling the quantity and/or rate of delivery of the deliverable agent received by the user.

The deliverable agent may therefore be provided in a mixture containing one or more evaporation enhancing agents, i.e. agents which enhance the vapour formation of a vapour of the deliverable agent. Suitable evaporation enhancing agents include glycerin, vegetable glycerin (VG), propylene glycol, polyethylene glycol or mixtures thereof.

However, the devices of the invention may advantageously afford a method by which the deliverable agent may be delivered to the user without the requirement for evaporation enhancing agents, such as those above, which may potentially be toxic or which may degrade during the heating process to form toxic by-products. Thus, in a preferred embodiment, the deliverable agent is provided (in the carrier material) either alone or in a mixture which does not contain any of the above-mentioned evaporation enhancing agents.

In another embodiment, the deliverable agent may be provided in a mixture containing one or more additional substances which are not intended to provide any therapeutic benefit to the user. By way of example, said additional substances may be present in order to aid in the manufacture of the product, to aid in the vaporisation of the deliverable agent, or to improve the experience for the user.

The aerosol or vapour that is delivered to the user consists essentially of air, the deliverable agent (e.g. active pharmaceutical ingredient) and potentially one or more optional additional substances (e.g. an evaporation enhancing agent) that may be present in admixture with the deliverable agent.

For example, the aerosol or vapour may also contain any desired flavouring agent (e.g. a flavouring or sweetener as described herein) or inert additive for improving the taste, consistency or texture of the aerosol or vapour, thereby making the inhalation therapy more palatable to the user (i.e. the patient).

In one embodiment, the deliverable agent is nicotine. Nicotine is typically obtained from tobacco products, e.g. tobacco oil and other extracts, and is usually present in such products as nicotine bitartrate. Both nicotine and nicotine bitartrate may be used in the inhalation devices described here.

Inhalation devices containing nicotine may be used in the treatment of nicotine dependence, (e.g. nicotine addiction) with a view to aiding an individual in reducing smoking or stopping altogether.

Inhalation devices which contain apparatus which is capable of monitoring the usage of the device, and possibly restricting use by the user, may also be particularly advantageous for use in treating nicotine dependence. Such devices may aid the user in recording their usage patterns, and thereby more accurately controlling their usage over time.

More broadly, the deliverable agent may be an active pharmaceutical ingredient. An active pharmaceutical ingredient is a pharmaceutical ingredient that is intended to be administered to a patient in need thereof in order to provide a therapeutic benefit or effect.

For example, the active pharmaceutical ingredient may be nicotine, and may be intended for use in therapeutic treatments as described above. In a preferred embodiment, the active pharmaceutical ingredient is not nicotine (or a pharmaceutically-acceptable salt thereof). The devices of the present invention may also be configured to deliver a plurality of active pharmaceutical ingredients to the user. Thus, in a further embodiment, the inhalation of the devices of the present invention contain a plurality of active pharmaceutical ingredients.

Active pharmaceutical ingredients that may be employed in devices of the invention preferably include substances from various pharmacological classes, e.g. antibacterial agents, antihistamines and decongestants, anti-inflammatory agents, antiparasitics, antivirals, local anaesthetics, antifungals, amoebicidals or trichomonocidal agents, analgesics, antianxiety agents, anticlotting agents, antiarthritics, antiasthmatics, anticoagulants, anticonvulsants, antidepressants, antidiabetics, antiglaucoma agents, antimalarials, antimicrobials, antineoplastics, antiobesity agents, antipsychotics, antihypertensives, auto-immune disorder agents, anti-impotence agents, anti-Parkinsonism agents, anti-Alzheimer's agents, antipyretics, anticholinergics, anti-ulcer agents, blood-glucose-lowering agents, bronchodilators, central nervous system agents, cardiovascular agents, cognitive enhancers, contraceptives, cholesterol-reducing agents, agents that act against dyslipidermia, cytostatics, diuretics, germicidials, H2 blockers, proton pump inhibitors, hormonal agents, anti-hormonical agents, hypnotic agents, inotropics, muscle relaxants, muscle contractants, physic energizers, sedatives, sympathomimetics, vasodilators, vasocontrictors, tranquilizers, electrolyte supplements, vitamins, uricosurics, cardiac glycosides, membrane efflux inhibitors, membrane transport protein inhibitors, expectorants, purgatives, contrast materials, radiopharmaceuticals, imaging agents, opioids, peptides, enzymes, growth factors, vaccines, mineral trace elements. Particular classes of active pharmaceutical ingredients that may be mentioned include antihypertensives, sedatives, hypnotics, opioids (including those used as analgesics, sedatives or for the treatment of cough), and non-opioid analgesics.

Active pharmaceutical ingredients that may be employed in devices of the invention may be substances that are solids, liquids or gases under ambient conditions. For the avoidance of doubt, where more than one active pharmaceutical ingredient is employed in devices of the invention, those ingredients may be provided in the same or different physical state (e.g. one may be solid and another may be liquid). In embodiments in which one or more of the active pharmaceutical ingredients present in the device is a gas under ambient conditions, said gas may be provided in a form in which it is contained (e.g. dissolved or suspended) in a second substance wherein the mixture of the gas and the second substance may then be incorporated into the carrier material.

Active ingredients that may be employed in devices of the invention preferably include any that are open to abuse potential, such as those that are useful in the treatment of acute or chronic pain, attention deficit hyperactivity disorders (ADHD), anxiety and sleep disorders, as well as growth hormones (e.g. erythropoietin), anabolic steroids, etc. Where active ingredients that are open to abuse potential are used, it is particularly preferred that the ceramic material is one that is based on a chemically bonded ceramic or a geopolymer, as described above. A full list of potentially abusable substances may be found easily by the skilled person, for example see the active ingredients listed on the following weblink: www.deadiversion.usdoj.gov.

Non-opioid drug substances that may be specifically mentioned include non-opioid analgesics such as sumatriptan (and other 5-HT$_1$ agonists); salicylates, such as aspirin, aloxiprin, methyl salicylate, magnesium salicylate, ethyl salicylate, bismuth subsalicylate, sodium salicylate, salicylamide, salicin, benorilate, salsalate, ethenzamide, dflunisal, trolamine salicylate, homosalate, salicylmethylecgonine, octyl salicylate, aluminon, benzyl salicylate, copper aspirinate, and potassium salicylate; psychostimulants, such as modafinil, amphetamine, dextroamphetamine, methamphetamine and hydroxyamphethamine and, more preferably, methylfenidate; benzodiazepines, such as bromazepam, camazepam, chlordiazepoxide, clotiazepam, cloxazepam, delorazepam, estazolam, fludiazepam, flurazepam, halazepam, haloxazepam, ketazolam, lormetazepam, medazepam, nimetazepam, nordiazepam, oxazolam, pinazepam, prazepam, temazepam, tetrazepam and, more preferably, alprazolam, clonazepam, diazepam, flunitrazepam, lorazepam, midazolam, nitrazepam, oxazepam and triazolam; and other, non-benzodiazepine sedatives (e.g. short-acting hypnotics), such as zaleplon, zolpidem, zopiclone and eszopiclone.

Other non-opioid analgesics that may be mentioned include cannabis-derived analgesics particularly cannabinoid substances, and most particularly cannabinoid substances originating from cannabis plants. Cannabinoid substances having analgesic properties that may be mentioned include tetrahydrocannabinol, cannabidiol and cannabinol. Thus, inhalation devices containing one or more cannabinoid substances may also be used in medicine, particularly in the treatment of pain.

In embodiments in which the deliverable agent is an active pharmaceutical ingredient, the deliverable agent should be a heat-stable pharmaceutical substance, preferably one which is stable at temperatures up to at least about 400° C., more preferably up to at least about 600° C. By the use of the term "heat-stable", it is meant that the deliverable agent is sufficiently stable at that temperature to ensure that it would not undergo significant chemical degradation during use, e.g. when the deliverable agent is a heat-stable pharmaceutical substance then "heat stable" refers to pharmaceutical substances which exhibit not more than 5% degradation when heated to 200° C. for 30 seconds.

The devices of the present invention may be used to deliver active pharmaceutical ingredients which having a boiling point of up to at least 600° C. It is preferred that the pharmaceutical substance has a boiling point that is at or below about 400° C., such as at or below about 300° C., preferably at or below about 200° C.

Devices of the invention may also find utility in the formulation of pharmaceuticals where crushing of a tablet may put the patient at risk, or may increase the risk for adverse effects and/or an unpleasant taste. That is to say, those active ingredients where avoidance of one or more of the following is desirable:

i) a tablet being chewed before being swallowed;

ii) accidental destruction during passage through the gastrointestinal tract; and/or iii) ex vivo tampering, i.e. crushing for subsequent abuse (vide infra), or for ease of subsequent swallowing, which may result in destruction of the functionality of the formulated drug.

Such drugs will be well known to the skilled person, but may also be found for example on the weblink www.ismp.org.

However, preferred pharmaceutically-active ingredients that may be employed in devices of the invention include opioid analgesics. It is particularly preferred that the ceramic material is one that is based on a chemically bonded ceramic or, most preferably, a geopolymer when the inhalation device contains an opioid analgesic. The term "opioid analgesic" will be understood by the skilled person to include any substance, whether naturally-occurring or synthetic, with opioid or morphine-like properties and/or which binds to opioid receptors, particularly the μ-opioid receptor, having at least partial agonist activity, thereby capable of producing an analgesic effect. The problems of potential formulation tampering and drug extraction by drug addicts are particularly prominent with opioids.

Opioid analgesics that may be mentioned include opium derivatives and the opiates, including the naturally-occurring phenanthrenes in opium (such as morphine, codeine, thebaine and Diels-Alder adducts thereof) and semisynthetic derivatives of the opium compounds (such as diamorphine, hydromorphone, oxymorphone, hydrocodone, oxycodone, etorphine, nicomorphine, hydrocodeine, dihydrocodeine, metopon, normorphine and N-(2-phenylethyl)normorphine). Other opioid analgesics that may be mentioned include fully synthetic compounds with opioid or morphine-like properties, including morphinan derivatives (such as racemorphan, levorphanol, dextromethorphan, levallorphan, cyclorphan, butorphanol and nalbufine); benzomorphan derivatives (such as cyclazocine, pentazocine and phenazocine); phenylpiperidines (such as pethidine (meperidine), fentanyl, alfentanil, sufentanil, remifentanil, ketobemidone, carfentanyl, anileridine, piminodine, ethoheptazine, alphaprodine, betaprodine, 1-methyl-4-phenyl-1,2,3,6-tetrahydropyridine (MPTP), diphenoxylate and loperamide), phenylheptamines or "open chain" compounds (such as methadone, isomethadone, propoxyphene and levomethadyl acetate hydrochloride (LAAM)); diphenylpropylamine derivatives (such as dextromoramide, piritramide, bezitramide and dextropropoxyphene); mixed agonists/antagonists (such as buprenorphine, nalorphine and oxilorphan) and other opioids (such as tilidine, tramadol and dezocine). Further opioid analgesics that may be mentioned include allylprodine, benzylmorphine, clonitazene, desomorphine, diampromide, dihydromorphine, dimenoxadol, dimepheptanol, dimethylthiambutene, dioxaphetyl butyrate, dipipanone, eptazocine, ethylmethylthiambutene, ethylmorphine, etonitazene, hydroxypethidine, levophenacylmorphan, lofentanil, meptazinol, metazocine, myrophine, narceine, norpipanone, papvretum, phenadoxone, phenomorphan, phenoperidine and propiram.

More preferred opioid analgesics include morphine, oxycodone, buprenorphine, alfentanil, sufentanil, remifentanil and, particularly, fentanyl.

Active ingredients listed above may be formulated in devices of the invention in any specific combination.

The devices of the present invention are capable of being used with essentially any active pharmaceutical ingredient, or combination of ingredients, and the utility is not limited solely to the active pharmaceutical ingredient described or exemplified herein.

Active ingredients may further be employed in salt form or any other suitable form, such as e.g. a complex, solvate or prodrug thereof, or in any physical form such as, e.g., in an amorphous state, as crystalline or part-crystalline material, as co-crystals, or in a polymorphous form or, if relevant, in any stereoisomeric form including any enantiomeric, diastereomeric or racemic form, or a combination of any of the above.

Pharmaceutically-acceptable salts of active ingredients that may be mentioned include acid addition salts and base addition salts. Such salts may be formed by conventional means, for example by reaction of a free acid or a free base form of an active ingredient with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of active ingredient in the form of a salt with another counter-ion, for example using a suitable ion exchange resin.

Examples of pharmaceutically-acceptable addition salts include those derived from mineral acids, such as hydrochloric, hydrobromic, phosphoric, metaphosphoric, nitric and sulphuric acids; from organic acids, such as succinic acid, and particularly tartaric, acetic, citric, malic, lactic, fumaric, benzoic, glycolic, gluconic, succinic, arylsulphonic acids; and from metals such as sodium, magnesium, or preferably, potassium and calcium. In embodiments in which the active ingredient is nicotine, a particular salt that may be mentioned is nicotine bitartrate. References herein to "nicotine" include references to pharmaceutically-acceptable nicotine salts such as nicotine bitartrate, unless specified otherwise.

The devices of the invention may also be configured to allow the user to monitor and/or record their usage of the device over an undefined period of time. This may aid the user and medical professionals in accurately recording the amount and frequency at which the deliverable agent (i.e. the one or more active pharmaceutical ingredients) has been administered to the user.

In a further embodiment, the devices of the invention may comprise apparatus for recording the usage history of the device over a defined period of time. Such apparatus may comprise an electronic device which records the relevant events such as the total number of uses of the device, the number of times that the device has been refilled (e.g. the number of times that a cartridge has been replaced), the times at which the device is used or refilled, the amount of active ingredient that has been delivered to the user, and the like. Such data may be stored on the device so that it may be downloaded to a separate data processing device by the user or a medical professional, or the device may further comprise a display unit so that the data may be visually displayed.

In a further embodiment, the device may comprise an interface or a data transmission unit to allow the recorded data to be extracted from the device for separate analysis. A suitable interface includes a Universal Serial Bus (USB) or another similar component allowing an electrical connection suitable for data transfer. In devices which contain a data transmission unit, said data may be transmitted by the device, e.g. via Bluetooth or similar, to a separate device. In each case, the separate device may be an electronic data processing device which contains suitable software (e.g. an app) for processing the data received from the inhalation device.

In a yet further embodiment, the device may be configured to monitor the usage by the user, and optionally control the extent to which the deliverable agent is administered to the user. For example, the device may be configured so that the number of times that it may be used in a specific period may be restricted. This is particularly useful where it is inadvisable for the user to be able to receive a large quantity of the deliverable agent (e.g. active pharmaceutical ingredient) over a given period of time, e.g. if the deliverable agent is addictive or toxic, or if the device is intended for use by children or the mentally impaired. Such devices may therefore allow metering of the amount of deliverable agent that is being administered to the user.

Protective coatings may also be used in conjunction with the carrier materials of the presently disclosed devices.

Protective coatings may be used to help control the rate of vaporisation of the deliverable agent during use. One or more coatings may be applied to the external surface of the carrier material. When the carrier material is heated during use, the coating may help to control the temperature at which evaporation occurs. This, in turn, may further aid in controlling the delivery of the deliverable agent, for example by ensuring that the user receives the vaporised material in a short period of time and thereby reducing the likelihood that the user may cease inhaling before having received the entire intended dose.

Protective coatings may also be useful in improving the stability of the deliverable agents within the device. For example, the coating may shield the one or more of the deliverable agents from the external environment, or it may act as a barrier between deliverable agents thereby reducing the extent to which they may mix and chemically interact with each other.

Alternatively, a protective coating may contain a second active pharmaceutical ingredient which has additional useful properties (e.g. the second active pharmaceutical ingredient may be an antidote to the first active pharmaceutical ingredient). In an illustrative example, the first active pharmaceutical ingredient may be a therapeutic agent that is open to abuse potential. A suitable antidote (e.g. a pharmaceutical antagonist) is then chosen having a higher boiling point than the first active pharmaceutical ingredient. When such a mixture is used within the devices of the invention, the heating of the carrier material may be controlled to ensure that the user receives a sufficient amount of the first active pharmaceutical ingredient while receiving only a minimal amount of the antidote. Said mixtures may be resistant to abuse insofar as the use of a poorly controlled heat source, e.g. a naked flame, would result in the simultaneous release of the first active pharmaceutical ingredient and the antidote.

The carrier material that is used in the devices of the invention may be designed to be inert in the following ways:

(a) general physico-chemical stability under normal storage conditions, including temperatures of between about minus 80 and about plus 50° C. (preferably between about 0 and about 40° C. and more preferably room temperatures, such as about 15 to about 30° C.), pressures of between about 0.1 and about 2 bars (preferably at atmospheric pressure), relative humidities of between about 5 and about 95% (preferably about 10 to about 75%), and/or exposure to about 460 lux of UV/visible light, for prolonged periods (i.e. greater than or equal to six months). Under such conditions, carrier material networks as described herein may be found to be less than about 5%, such as less than about 1% chemically degraded/decomposed, as above;

(b) particularly importantly when the active ingredient that is employed is an opioid analgesic, general physico-chemical stability under acidic, alkaline and/or alcoholic (e.g. ethanolic) conditions at room temperature and/or under at elevated temperatures (e.g. up to about 200° C.), which may result in less than about 15% degradation, so avoiding the possibility of deliberate ex vivo extraction of drug for intended abuse (e.g. by acid or alcohol extraction, followed by injection, or heating the ceramic component of the devices of the invention and then an opioid addict inhaling the vapour or smoke that is given off); and (c) again, particularly importantly when the active ingredient that is employed is an opioid analgesic, general physical stability so reducing the possibility of mechanical grinding or milling with a view to extraction of active ingredient as defined in (b) above, or by an opioid addict sniffing a resultant powder directly.

With reference to (c) above, it is preferred in this respect that the network exhibits a compressive strength of greater than about 1 MPa, such as greater than about 5 MPa, e.g. about 10 MPa on micro- and nano-structure level, which is high enough to withstand breakdown of the material at the microstructure level, i.e. of less than about 200 µm.

The ceramic material containing the deliverable agent may be prepared by way of a variety of routine techniques, and using standard equipment, known to the skilled person, including mixing together the deliverable agent and the carrier material or its precursors.

Standard mixing equipment may be used for mixing together components of compositions of the invention. The mixing time period is likely to vary according to the equipment used, and the skilled person will have no difficulty in determining by routine experimentation a suitable mixing time for a given combination of ingredient(s).

The deliverable agent may be mixed with the carrier material (e.g. ceramic) by way of a variety of techniques, such as introduction by way of a sol-gel process, as a solution, a slurry, a paste or a putty. The introduction of the mixture comprising the deliverable agent and a carrier material (or precursor(s) thereto) may be followed by some sort of "curing" to form the pores in which the deliverable agent resides. It is during this process that the porous carrier material network may be formed.

A preferred process for the formation of carrier material for use in devices of the invention involves the mixing together of a carrier material (e.g. a ceramic material or precursor(s) thereto) and deliverable agent, and then adding a liquid, such as an aqueous solvent (e.g. water), so providing a wet granulate.

Another preferred process for the formation of carrier material for use in devices of the invention involves the mixing together of a deliverable agent with an aqueous solvent (e.g. water), before combining this mixture with a carrier material (e.g. a ceramic material or precursor(s) thereto).

Wet granulation techniques are well known to those skilled in the art and include any technique involving the massing of a mix of dry primary powder particles using a granulating fluid, which fluid comprises a volatile, inert solvent, such as water, optionally in the presence of a pelletisation aid material.

The product obtained by the above-mentioned process may further be adapted by:

(I) extrusion of the granulate (in cases where granulation takes place);

(II) spheronisation (forcing a wet mass through a sieve to produce pellets);

(III) drying; and/or (IV) (if necessary) hardening by way of heat, using routine techniques in all cases.

In the process for formation of carrier materials comprising geopolymers for use in devices of the invention, preformed geopolymer may be reacted together with further aluminosilicate precursor and aqueous alkaline liquid (e.g. solution), preferably in the presence of a source of silica (as hereinbefore described), also in the presence of the deliverable agent as hereinbefore described. For compositions of the invention comprising geopolymers, curing may be performed by allowing the resultant mixture to harden into any given shape, e.g. blocks, pellets, granules or a powder. In this respect, the mixture may be transferred into moulds and left to set as pellets/granules or alternatively (e.g. preferably) pellets/granules may be manufactured using an appropriate extrusion-spheronisation technique. Here, the formed paste (powder and liquid mixture) may be extruded through an orifice. The size of the orifice may be from about 10 µm up to about 30 mm, preferably from about 100 µm to about 1 mm. If larger pellets/granules are required, the size of the orifice may be larger, e.g. from about 1 mm up to about 30 mm, or preferably from about 1 mm up to about 10 mm. The formed extrudate may then be placed in a spheroniser, which is typically a vertical hollow cylinder with a horizontal rotating disk located inside. When the disk is spun, the extrudate is broken into uniform lengths and gradually formed into spherical pellets, which may then be left to harden as described hereinbefore.

In the processes described above, primary particles of the deliverable agent (e.g. the opioid analgesic) may be processed by techniques, such as grinding, dry milling, wet milling, precipitation, etc, prior to granulation.

In all cases, suitable pellet/granule sizes are in the range of about 0.05 mm to about 3.0 mm (e.g. about 2.0 mm, such as about 1.7 mm), and preferably about 0.1 mm (e.g. about 0.2 mm) to about 1.6 mm (e.g. about 1.5 mm), such as about 1.0 mm.

Carrier materials for use in devices of the invention may further comprise one or more further commonly-employed pharmaceutical excipients. Suitable excipients include inactive substances that are typically used as a carrier for active ingredients in medications. Suitable excipients also include those that are employed in the pharmaceutical arts to bulk up pharmaceutical compositions that employ very potent active ingredients, to allow for convenient and accurate dosing. Alternatively, excipients may also be employed in manufacturing processes of the compositions of the invention to aid in the handling of the active ingredient concerned.

In this respect, pharmaceutically-acceptable excipients include filler particles, by which we include particles of material that do not take participate chemically in the process during which the carrier material that is used in the devices of the invention is formed. Such filler particles may be added as ballast and/or may provide the composition with functionality. Non-limiting examples include: zirconium dioxide and barium sulfate to increase radio-opacity, which may be added to smaller particles (e.g. milled) of carrier material used in the devices of the invention. The amount of added filler particles may be up to about 80 wt %, preferably up to about 40 wt % of the weight of the carrier material. Preferably the total volume of the filler is relatively small (e.g. below about 50% by volume of the entire carrier material structure (including pores)) in order to ensure that the carrier material retains a sufficient mechanical strength.

Additional pharmaceutically-acceptable excipients include carbohydrates and inorganic salts such as sodium chloride, calcium phosphates and calcium carbonate.

The carrier material may alternatively be milled to a fine powder, preferably with a powder grain size of below about 100 μm, and more preferably below about 20 μm. Carrier materials with grain sizes below 1 μm may be used in the devices of the invention, but preferred grain sizes are in the region of about 10 μm. Milling is optionally performed using ball-milling, planetary ball-milling, jet milling or a combination thereof.

In the aforementioned embodiments, the carrier material may further include a pelletisation aid material. A pelletisation aid material may be defined as a material that is capable of controlling the distribution of granulating liquid through the wet powder mass during pelletisation and to modify the rheological properties in the mixture. Suitable pelletisation aid materials include hydroxypropylmethylcellulose (HPMC), hydroxyethylcellulose (HEC) and, preferably, microcrystalline cellulose. If present, the pelletisation aid material is preferably employed in an amount of between 0.5 and 50% by weight based upon the total weight of the tablet formulation. A preferred range is from 1 to 20%, such as from about 2.0 to about 12% (e.g. about 10%) by weight.

The carrier material used in the devices of the invention may also optionally contain bulking agents, porogens, dispersion agents or gelating agents to control the rheology and porosity. The total amount of such excipients is limited to about 20 wt % of the total weight of the carrier material (i.e. the ceramic or geopolymeric material) including any other components that may be present (e.g. active pharmaceutical ingredients, bulking agents, etc.). Non-limiting examples of such excipients include polycarboxylic acids, cellulose, polyvinylalchol, polyvinylpyrrolidone, starch, nitrilotriacetic acid (NTA), polyacrylic acids, PEG, sorbitol, mannitol, glycerol, pharmaceutically-acceptable oils (including vegetable oils (olive oil, maize oil, corn oil, peanut oil, sunflower oil, flaxseed oil, palm oil, castor oil, soybean oil, etc.), essential oils (e.g. evening primrose oil), omega 3 oils (e.g. fish oils), paraffin oil, lipid oils derived from animal issue, silicone oils, etc.), and combinations thereof.

The carrier material may also comprise one or more binders. A binder may be defined as a material that is capable of acting as a bond formation enhancer, facilitating the incorporation of the deliverable agent into the carrier material. Suitable binders include cellulose gum and microcrystalline cellulose. If present, binder is preferably employed in an amount of between 0.5 and 20% by weight based upon the total weight of the carrier material and the materials contain therein. A preferred range is from 1 to 15%, such as from about 2.0 to about 12% (e.g. about 10%) by weight.

The carrier material may also comprise one or more taste masking agents, flavourings (e.g. lemon, peppermint powder or, preferably, menthol), or sweeteners (e.g. neohesperidin, acesulfame K or, preferably, sucralose).

The carrier materials may also comprise one or more colourants (e.g. iron oxide for red, cobalt for blue, titanium oxide for white, and so forth). Those colourants would typically be provided in the form of particles of said coloured material with an appropriate size to enable the colour to be visible without significantly affecting the ability of the carrier material to store the deliverable agent and release it upon heating. As with all of the additives discussed above, the particles of colourant may be added to the mixture of ceramic precursor materials before that mixture is cured or hardened.

The devices of the present invention may be used to deliver one or more deliverable agents to a user. Thus, in a third aspect of the invention there is provided a method of delivering a deliverable agent in the form of a vapour or aerosol to a user, which method comprises:

providing an article comprising:

(i) a solid, porous carrier material as defined herein having a porosity of at least 10%; and (ii) a deliverable agent as defined herein located within the pores of the carrier material; and heating the carrier material to vaporise the deliverable agent.

In one embodiment, the article is an inhalation device as defined herein. In an alternative embodiment, the article is a cartridge or formulation that is suitable for use in an inhalation device as defined herein. Thus, in a fourth aspect of the invention there is provided an article as defined herein. In embodiments in which the article is a cartridge that is suitable for use in an inhalation device as defined herein which contains a heating element, it is preferred that the cartridge is shaped to fit with the heating element.

In a further embodiment, there is provided the use of the article as defined above in the delivery of a deliverable agent in the form of a vapour or aerosol to a user. Similarly, said use will involve the step of heating the carrier material in order to vaporise the deliverable agent to allow it to be inhaled by the user.

In other particular embodiments of the third aspect of the invention, particularly in embodiments in which the device is configured to monitor the usage of the device by the user, and optionally control the extent to which the deliverable agent may be administered to the user, the method may involve the administration of a controlled dosage of the deliverable agent to the user. This is particularly useful where the deliverable agent is addictive or toxic, or if the device is intended for use by children or the mentally impaired. Particular examples include methods in which the deliverable agent is an opioid analgesic.

When the deliverable agent is an active therapeutic agent, the delivery of that agent to the user may be intended for the treatment of a disease or condition. For the avoidance of doubt, by "treatment" we include the therapeutic treatment, as well as the symptomatic treatment, the prophylaxis, or the diagnosis, of the condition.

Thus, in a fifth aspect of the invention there is provided a method of treating or preventing a disease comprising using an inhalation device as hereinbefore described (e.g. wherein the deliverable agent is an active pharmaceutical ingredient) to deliver an active pharmaceutical ingredient in the form of an aerosol or vapour to a subject in the need thereof (i.e. to a person suffering from or susceptible to said disease), wherein said active pharmaceutical ingredient treats or prevents said disease.

The inhalation devices of the present invention may be effective for use in anaesthesia. In such embodiments, the devices of the invention may be used to deliver a controlled quantity of one or more anaesthetic agents to a patient in order to give the desired therapeutic effect, be it analgesia, muscle relaxation, hypnosis, or any combination thereof.

Inhalation devices of the invention comprising opioid analgesics are useful in the treatment of pain, particularly severe and/or chronic pain. According to a further embodiment, there is provided a method of treatment of pain which method comprises using an inhalation device as hereinbefore described to deliver one or more opioid analgesics in the form of an aerosol or vapour to a person suffering from or susceptible to pain.

Inhalation devices of the invention comprising non-opioid analgesics may also be useful in the treatment of pain. In embodiments in which the active pharmaceutical ingredient is sumatriptan succinate, the device may be useful in treating migraine. Delivery of an analgesic via inhalation is particularly effective at providing rapid relief of pain, particularly in sufferers of migraine. By contrast, oral delivery of analgesics typically cannot provide such rapid relief.

In a further aspect of the invention there is provided a method of treating pain wherein the method involves using an inhalation device of the present invention in which the deliverable agent is cannabis-derived analgesic, such as any of the cannabinoid substances mentioned herein.

In a further aspect of the invention there is provided a method of treating nicotine dependence (e.g. nicotine addiction) wherein the method involves using an inhalation device of the present invention in which the deliverable agent is nicotine (or a pharmaceutically-acceptable salt thereof) to deliver nicotine in the form of an aerosol or vapour to a person suffering from symptoms of nicotine dependence. Similarly, the devices of the invention may be useful in a method of treating (e.g. alleviating) the symptoms of nicotine dependence (including nicotine addiction or nicotine withdrawal). Such symptoms may include cravings for nicotine, anger/irritability, anxiety, depression, impatience, trouble sleeping, restlessness, hunger or weight gain, and/or difficulty concentrating.

Nicotine may also be used to ameliorate symptoms associated with various diseases, including dementia, Alzheimer's disease, Parkinson's disease, Huntington's disease, and depression. Thus, in a yet further aspect of the invention there is provided a method of ameliorate symptoms associated with dementia, Alzheimer's disease, Parkinson's disease, Huntington's disease, and depression, wherein the method involves using an inhalation device of the present invention in which the deliverable agent is nicotine (or a pharmaceutically-acceptable salt thereof) to deliver nicotine in the form of an aerosol or vapour to a person suffering from said symptoms.

Inhalation devices of the present invention which contain an active pharmaceutical ingredient are capable of releasing a pharmacologically effective amount of the active ingredient during normal use. By "pharmacologically effective amount", we refer to an amount of active ingredient, which is capable of conferring a desired therapeutic effect on a treated patient, whether administered alone or in combination with another active ingredient. Such an effect may be objective (i.e. measurable by some test or marker) or subjective (i.e. the subject gives an indication of, or feels, an effect).

More preferred compositions of the invention may be adapted (for example as described herein) to provide a sufficient dose of drug over the dosing interval (irrespective of the number of doses per unit time) to produce a desired therapeutic effect.

The amounts of active ingredients that may be employed in devices of the invention may thus be determined by the physician, or the skilled person, in relation to what will be most suitable for an individual patient. This is likely to vary with the type and severity of the condition that is to be treated, as well as the age, weight, sex, renal function, hepatic function and response of the particular patient to be treated.

In one embodiment of the invention, the device is intended for a single use, and contains sufficient quantity of the active pharmaceutical ingredients to allow no more than about one unit dose of that ingredient to be delivered to the recipient via inhalation. Alternatively, in embodiments in which the carrier material and active pharmaceutical ingredient are supplied together in a cartridge or unit, each cartridge or unit may contain sufficient quantity of the active pharmaceutical ingredients to allow no more than about one dose of that ingredient to be delivered to the recipient via inhalation.

Suitable dosages of active ingredient in one inhalation delivery unit (e.g. a single cartridge containing the carrier material and active ingredient) may be below 1 g, preferably below 100 mg and above 1 µg. Where the deliverable agent is an opioid analgesic (e.g. fentanyl), or another abusable substance, the devices, cartridges and formulation units described herein may advantageously contain only a single dose unit of that deliverable agent. The use of chemically bonded ceramics and geopolymers as carrier materials greatly improves the ability to control the amount of drug that is stored in the device (or cartridge, etc.) and/or that is delivered to the patient compared to formulations in which the drug is stored as a liquid. Additionally, such single-dose formulations (particularly those in which the carrier material is based on a geopolymer) are also far less prone to abuse.

In embodiments in which the deliverable agent is nicotine, suitable daily dosages may be from about 1 to about 100 mg/day. Conventional cigarettes typically contain between about 8 and 20 mg nicotine. It is preferred that the devices and cartridges disclosed herein contain an amount of nicotine that is at least equivalent to one cigarette. When the nicotine is supplied to the patient in the form of replaceable cartridges (e.g. tablets, pellets or sticks), then each cartridge may contain from about 8 mg to about 20 mg of nicotine. As the devices may be capable of delivering substantially all of the nicotine held within the carrier material to the patient, each cartridge or device may advantageously contain a lower amount of nicotine (e.g. from about 100 µg to about 5 mg, or preferably from about 1 mg to about 3 mg) while still being able to deliver an amount of nicotine to the patient that is approximately equivalent to that inhaled when smoking a single cigarette. Higher quantities nicotine may also be held in a single device or cartridge, e.g. up to 100 mg, up to 500 mg or up to 1 g. Such devices and cartridges would be intended to be used multiple times, either over a single day or several days, before the device needs to be refilled or the cartridge needs to be refilled or replaced. Such quantities of nicotine may be used in devices, cartridges and formulation units which are used in medicine, e.g. in the treatment of nicotine dependence (e.g. nicotine addiction), treating (or alleviating) the symptoms of nicotine dependence (including nicotine addiction or nicotine withdrawal), dementia, Alzheimer's disease, Parkinson's disease, Huntington's disease, and depression. Suitable doses for the treatment of such diseases (typically via a nasal spray) may range from 5 to 15 mg/day. A device or cartridge according to the invention may therefore contain a sufficient amount for a single daily dose, or a fraction thereof (e.g. one half, one third or one quarter).

When compositions of the invention comprise opioid analgesics, appropriate pharmacologically effective amounts of such opioid analgesic compounds include those that are capable of producing (e.g. sustained) relief of pain when the device is used and the drug is administered via inhalation. Thus, the total amount of opioid analgesic active ingredient that may be employed in a device of the invention will depend upon the nature of the relevant active ingredient that is employed, but may be in the range of about 0.0005%, such as about 0.1% (e.g. about 1%, such as about 2%) to about 20%, such as about 10%, for example about 7%, by weight based upon the total weight of the carrier material. The amount of this active ingredient may also be expressed as the amount in a unit dosage. In such a case, the amount of opioid analgesic active ingredient that may be present may be sufficient to provide a unit dosage that is from about 1 µg (e.g. about 5 µg) to about 50 mg (e.g. about 15 mg, such as about 10 mg).

The above-mentioned dosages are exemplary of the average case; there can, of course, be individual instances where higher or lower dosage ranges are merited, and such are within the scope of this invention.

Devices of the invention comprising opioid analgesics are useful in the treatment of pain, particularly severe and/or chronic pain. They may be particularly effective as they provide an advantageously rapid onset of effect (e.g. at a rate that is more rapid than would occur through many other routes of administration, particularly oral administration). According to a further aspect of the invention there is provided a method of treatment of pain which method comprises the use of a device of the invention to administer an opioid analgesic via inhalation to a person suffering from, or susceptible to, such a condition.

For the avoidance of doubt, by "treatment" we include the therapeutic treatment, as well as the symptomatic treatment, the prophylaxis, or the diagnosis, of the condition.

Devices of the invention containing multiple dose units possess the advantage of the avoidance and/or reduction of the risk of either dose dumping (i.e. the involuntary release), or equally importantly the deliberate ex vivo extraction, of the majority (e.g. greater than about 50%, such as about 60%, for example about 70% and in particular about 80%) of the dose of the active ingredient(s) that is initially within the carrier material in the device of the invention, either in vivo (i.e. when a composition of the invention is administered to a patient) or ex vivo (i.e. into another medium outside the body), within a timeframe that is likely to give rise to undesirable consequences, such as adverse pharmacological effects (for example when such release occurs in vivo in an involuntary sense), or the potential for abuse of that active ingredient (for example when such release is deliberately effected ex vivo by an individual). Such dose dumping release may for example take place either in vivo or ex vivo within about 3 hours, such as within about 2 hours, for example within about 1 hour, and particularly within about 30 minutes.

The devices of the invention may provide protection against intentional mechanical breakdown of the carrier material, e.g. by traditional methods such as crushing, pestle and mortar, hammering etc. due to the carrier material having a high compressive strength level at the micro-level material.

Devices of the invention, and particularly the carrier materials that are used therein, may also have the advantage that they may be prepared using established pharmaceutical processing methods and may employ materials that are approved for use in foods or pharmaceuticals or of like regulatory status.

Carrier materials that are used in the devices of the invention may also have the advantage that they may be more efficacious than, be less toxic than, be faster acting than, be more potent than, produce fewer side effects than, be more easily absorbed than, and/or have a better pharmacokinetic profile than, and/or have other useful pharmacological, physical, or chemical properties over, pharmaceutical compositions known in the prior art, whether for use in the treatment of pain or otherwise. This is particularly the case for embodiments in which the device of the invention, or the carrier material (e.g. in the case of replaceable cartridges) does not comprise a traditional evaporation enhancing agent such as propylene glycol, glycerine or polyethylene glycol.

The use of the carrier materials described herein (particularly chemically bonded ceramics and geopolymers) affords for the provision of removable and replaceable units to be used in conjunction with heating devices to attain acceptable levels of release of deliverable agent under heating, while minimising the risk of exposure to the stored materials within, e.g. through leakage. The carrier materials are also easily manufactured without the need for high temperature sintering, and therefore additional elements such as conductors and magnets can be incorporated into the carrier material to aid in the heating process. The ability to incorporate the deliverable agent into the carrier material as the carrier material structure is formed also allows for greater control over the amount of deliverable agent present.

Wherever the word "about" is employed herein in the context of dimensions (e.g. values, temperatures, pressures (exerted forces), relative humidities, sizes and weights, particle or grain sizes, pore sizes, timeframes etc.), amounts (e.g. relative amounts (e.g. numbers or percentages) of particles, individual constituents in a composition or a component of a composition and absolute amounts, such as doses of active ingredients, numbers of particles, etc.), deviations (from constants, degrees of degradation, etc.) it will be appreciated that such variables are approximate and as such may vary by ±10%, for example ±5% and preferably ±2% (e.g. ±1%) from the numbers specified herein.

The invention is illustrated by the following examples in which.

EXAMPLES

Example 1

Oven Heating

Figure 1:
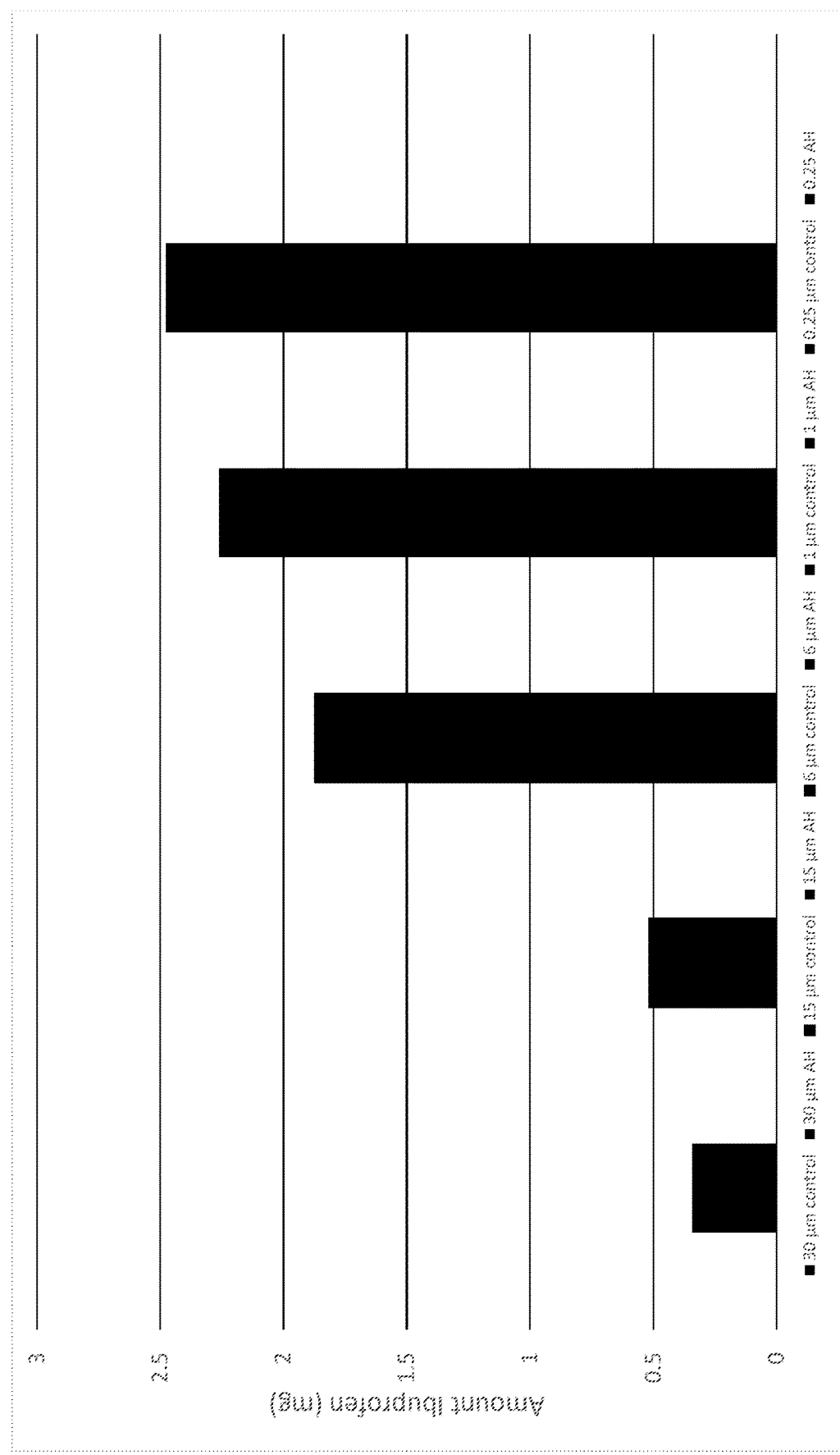
FIG. 1 shows the amount of ibuprofen in ceramic discs before (control) and after heat treatment (AH; n=1). Error bars show the maximum and minimum values.
Figure 2:
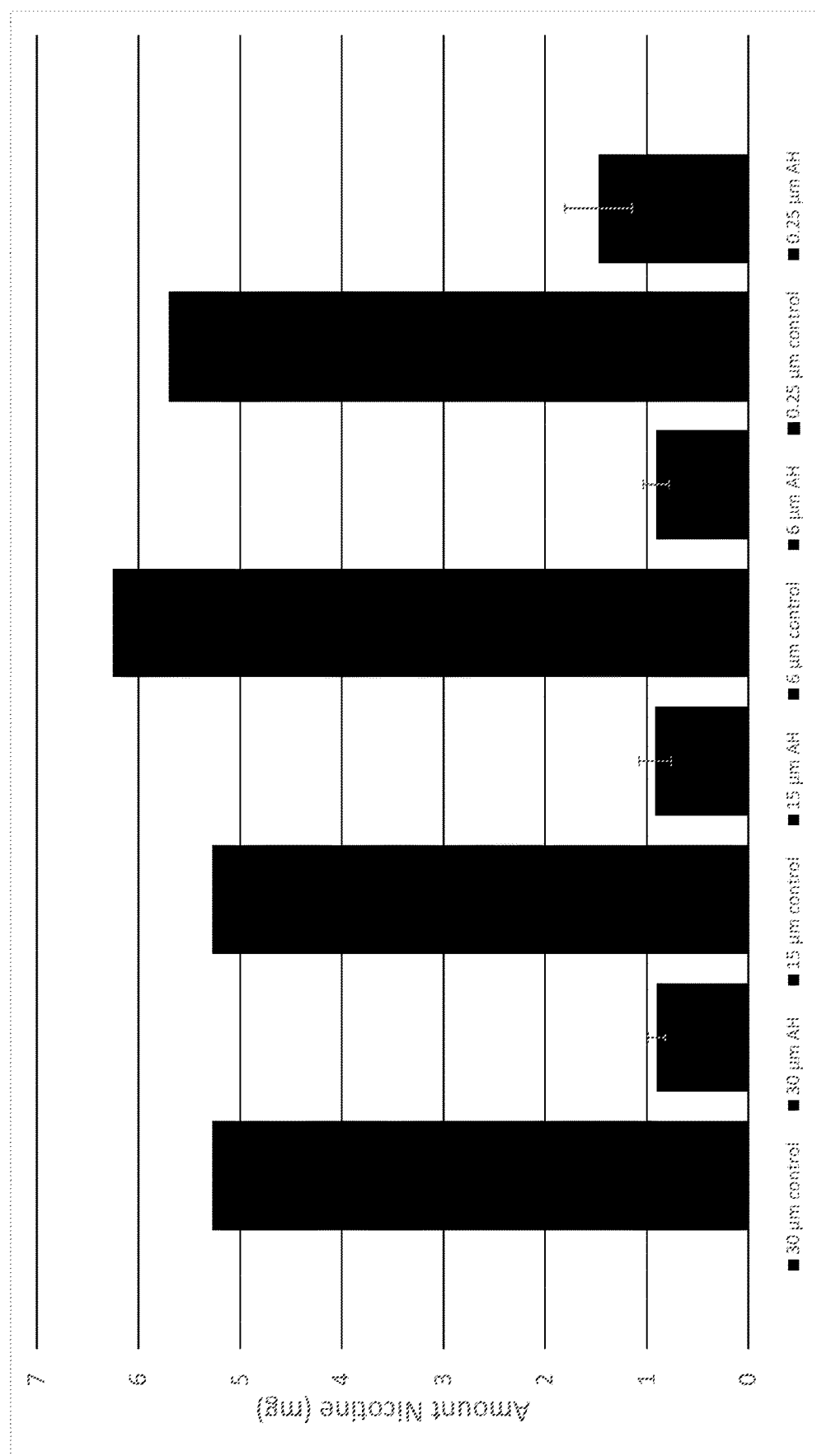
FIG. 2 shows the amount of nicotine in ceramic discs before (control; n=1) and after heat treatment (AH; n=2). Error bars show the maximum and minimum values.

Ceramic discs comprising ibuprofen (IOL Chemicals and Pharmaceuticals Ltd, India) were prepared using aluminium oxide ($Al_2O_3$; Keranova, Sweden) as follows.

Ceramic discs ($Al_2O_3$) with different pore sizes (0.25, 1, 6, 15 and 30 μm) were prepared in two sizes: (i) 63 mm in diameter and 6.3 mm in thickness (pore sizes 0.25, 1 and 6 μm); and (ii) 48 mm in diameter and 6.3 mm in thickness (pore sizes 15 and 30 μm). The porosity was approximately 40% vol and the density 3.75 g/cm$^3$ for all discs according to product specification.

The discs (pore sizes 0.25, 1, 6, 15 and 30 μm) were soaked in a 400 ml in phosphate buffer with pH 7.4 (one phosphate buffer saline tablet (Sigma-Aldrich, USA) dissolved in 200 ml deionized water) with a concentration of 408.5 μg/ml ibuprofen for 24 hours. The discs were dried in room temperature for 24 hours. The discs were heated in an oven at 250° C. for 15 minutes, the control discs were not heated. All discs were measured for concentration of ibuprofen in 400 ml phosphate buffer pH 7.4 at 37° C. (USP paddle method (paddle speed 50 rpm), VanKel 7025, Varian Inc, USA) and the concentration for ibuprofen was measured using a UV spectrophotometer Shimadzu 1800, Japan at a wavelength of 220 nm to determine the amount of ibuprofen in the ceramic discs. The amount of ibuprofen in control discs was measured after 15 hours (i.e. after maximum drug release) and in heat treated discs after 1.5 hours (i.e. the maximal amount drug was at this time point released).

The amount of ibuprofen remaining after heat treatment was zero for all samples. No significant changes in absorbance at other wavelengths were detected, indicating that no significant degradation of the ibuprofen had occurred.

Example 2

Oven Heating

Ceramic discs comprising nicotine (nicotine solution (24 mg/ml), Ritch Group Ltd, United Kingdom) were prepared using aluminium oxide ($Al_2O_3$; Keranova, Sweden) as follows.

Ceramic discs ($Al_2O_3$) with different pore sizes (0.25, 1, 6, 15 and 30 μm) were prepared in two sizes: (i) 63 mm in diameter and 6.3 mm in thickness (pore sizes 0.25, 1 and 6 μm); and (ii) 48 mm in diameter and 6.3 mm in thickness (pore sizes 15 and 30 μm). The porosity was approximately 40% vol and the density 3.75 g/cm$^3$ for all discs according to product specification.

A nicotine solution (0.25 ml; corresponding to 6 mg nicotine) was dispensed on the surface of the ceramic discs (pore sizes 0.25, 6, 15 and 30 μm). The discs were dried in room temperature for 24 hours. The discs were heated in an oven at 188° C. for 15 minutes, the control discs were not heated. All discs were measured for amount of nicotine in 400 ml phosphate buffer pH 7.4 at 37° C. (USP paddle method (paddle speed 50 rpm), VanKel 7025, Varian Inc, USA) and the concentration for nicotine was measured using a UV spectrophotometer Shimadzu 1800, Japan at a wavelength of 252.8 nm to determine the amount of nicotine in the ceramic discs. The amount of nicotine in control discs was measured after 15 hours (i.e. after maximum nicotine release) and in heat treated discs after 1.5 hours (i.e. the maximal amount nicotine was at this time point released).

The amount of nicotine remaining after heat treatment very significantly reduced for all samples compared to the pre-heat treatment control samples. No significant changes in absorbance at other wavelengths were detected, indicating that no significant degradation of the nicotine had occurred.

Example 3

Oven Heating

Aluminium Oxide Rods

Aluminium oxide ceramic rods were obtained from Ceramtech (Sweden): $Al_2O_3$ cylindrical rods, 3 mm diameter and 10 mm length containing 4 bore holes (oriented axially) having a diameter of 0.8 mm.

Calcium Sulphate Rods and Coins

Calcium sulphate alpha hemihydrate (CaS) rods were obtained from Bo Ehrlander AB (Sweden). Shaped silicon rubbers were used as molds for both rods (diameter: 6, length 12 mm) and coins (diameter: 12 mm, thickness: 2 mm). The calcium sulphate was mixed with deionised water (Liquid/Powder ratio of 0.4 (w/w)) to form a homogenous paste, which was filled in the rubber molds. When the paste was applied, the molds were set to dry for at least 12 h under ambient conditions.

Geopolymer Coins

Reagent grade kaolinite, fumed silica (7 nm particle size) and reagent grade sodium hydroxide were obtained from Sigma-Aldrich (Sweden). Sodium silicate solution was manufactured by dissolving sodium hydroxide (NaOH) and fumed silica ($SiO_2$) into deionised water. Metakaolin was formed by heating kaolinite for 2 hours in 800° C.

Geopolymer were synthesized by mixing sodium silicate solution with metakaolin using mortar and pestle until a uniform paste was formed. The composition of the geopolymer obtained the following molar ratios: Si/Al=1.94, $H_2O/Al_2O_3$=12.24 and $Na_2/Al_2O_3$=1.23. The paste was filled into coin shaped silicon rubber molds and hardened in 100% humidity for 48 hours at ambient pressure at 37° C. After curing, geopolymer were dried at ambient temperature and humidity for 24 hours.

Nicotine

Pure nicotine USP/EP was obtained from BGP Healthcare pvt. Ltd. (India). E-juice (LIQUA) 18 mg/ml and 24 mg/ml were obtained from Cigoteket (Sweden). E-juice is a solution of nicotine dissolved in propylene glycol. Concentrations below 18 mg/ml were achieved by adding an appropriate amount of deionised water to the e-juice.

Application of Nicotine

The application of nicotine was achieved by either soaking or dispensing nicotine or a nicotine solution in a range of concentrations onto the surface of the ceramic rod/coin.

Dispensing of Nicotine

Pure nicotine (in liquid form), pure E-juice or E-juice diluted with water was dispensed onto the surface of the rods or coins. After application of nicotine, the samples were dried for 24 hours in room temperature before heat treatment and/or analysis.

(ii) Soaking of Nicotine

The rods were soaked in pure nicotine or a nicotine solution (exact volume was not measured, but the rod was just covered with liquid, about 100 µl). The samples were soaked for 24 hours in room temperature and thereafter the samples were dried for 24 hours, before heat treatment and/or analysis.

Heating Method

Oven Wilfa EMK 218 was obtained from Wilfa, (Norway). The temperature was set to approximately 200° C. The temperature was measured using an IR-thermometer from Mastech.

Nicotine Release Detection

All nicotine release tests were carried out according to the same analytical method. The sample was immersed into a beaker containing 50 ml of deionised water. After 24 hours a sample was taken out and filtered (pore size: 0.2 µm). The sample was characterized by UV-spectrophotometer at a wavelength of 219 nm. The amount nicotine in the samples were then calculated. The difference in amounts in the reference sample and the heat treated sample was estimated to have evaporated.

The reference samples represent the amount of nicotine that was loaded before heat treatment. The difference in amount of nicotine detected in the heat-treated samples and the reference sample represents the amount of nicotine that evaporated during the heat treatment.

Results—Aluminium Oxide

Figure 3:
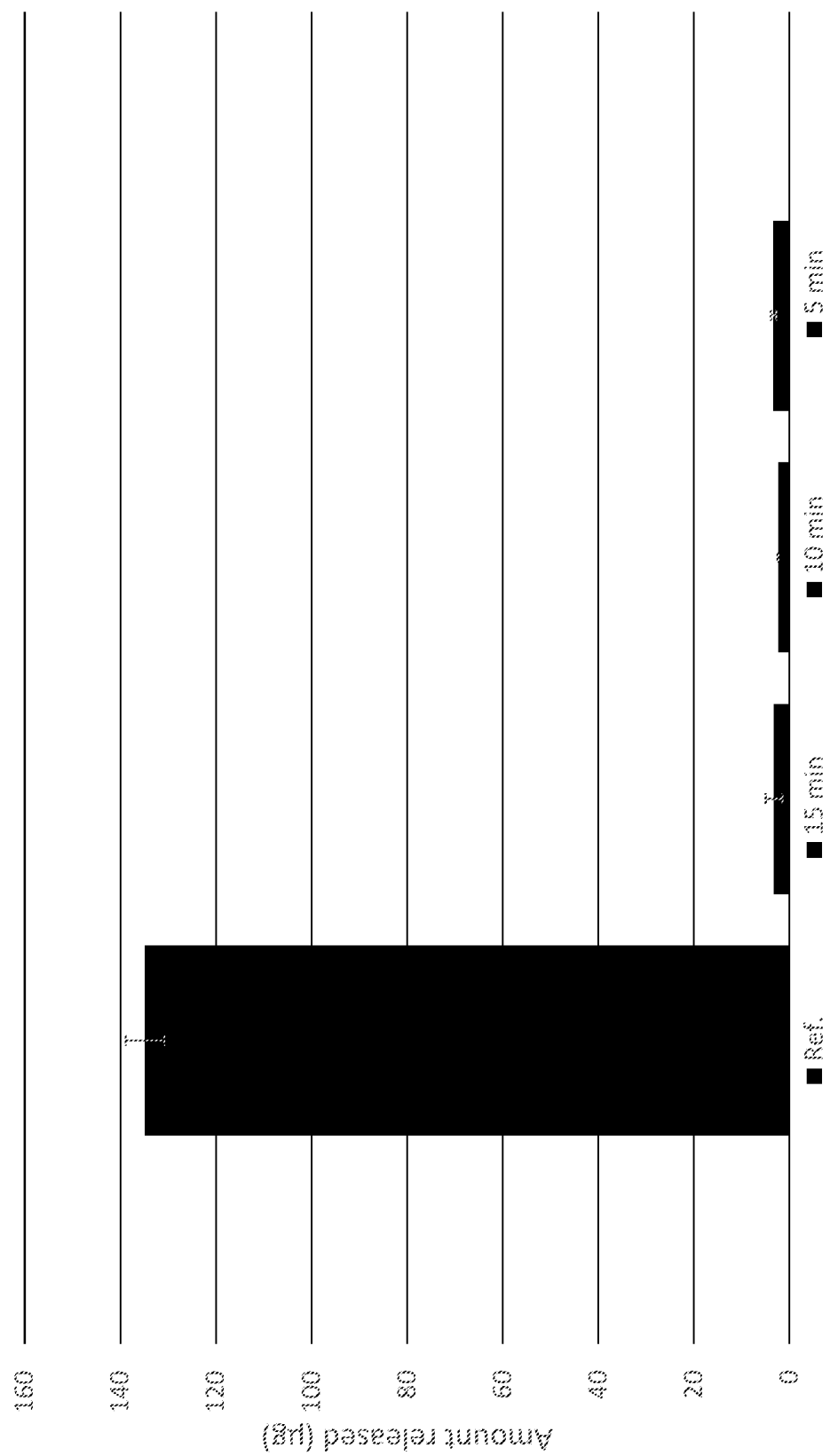
FIG. 3 shows the amount of nicotine in aluminium oxide rods before and after oven heat treatment (n=3)

Aluminium oxide rods were soaked in 6 mg/ml of nicotine solution (diluted e-juice) for 24 hours. The amount of nicotine remaining in the rods after before and heat treatment was measured, and is shown in FIG. 3.

When heated, almost all of the nicotine was released within the first 5-10 min, since the amount of nicotine remaining in the samples after heat treatment was low. The rods were able to absorb approximately 135 µg nicotine/rod.

Results—Calcium Sulphate

Figure 4:
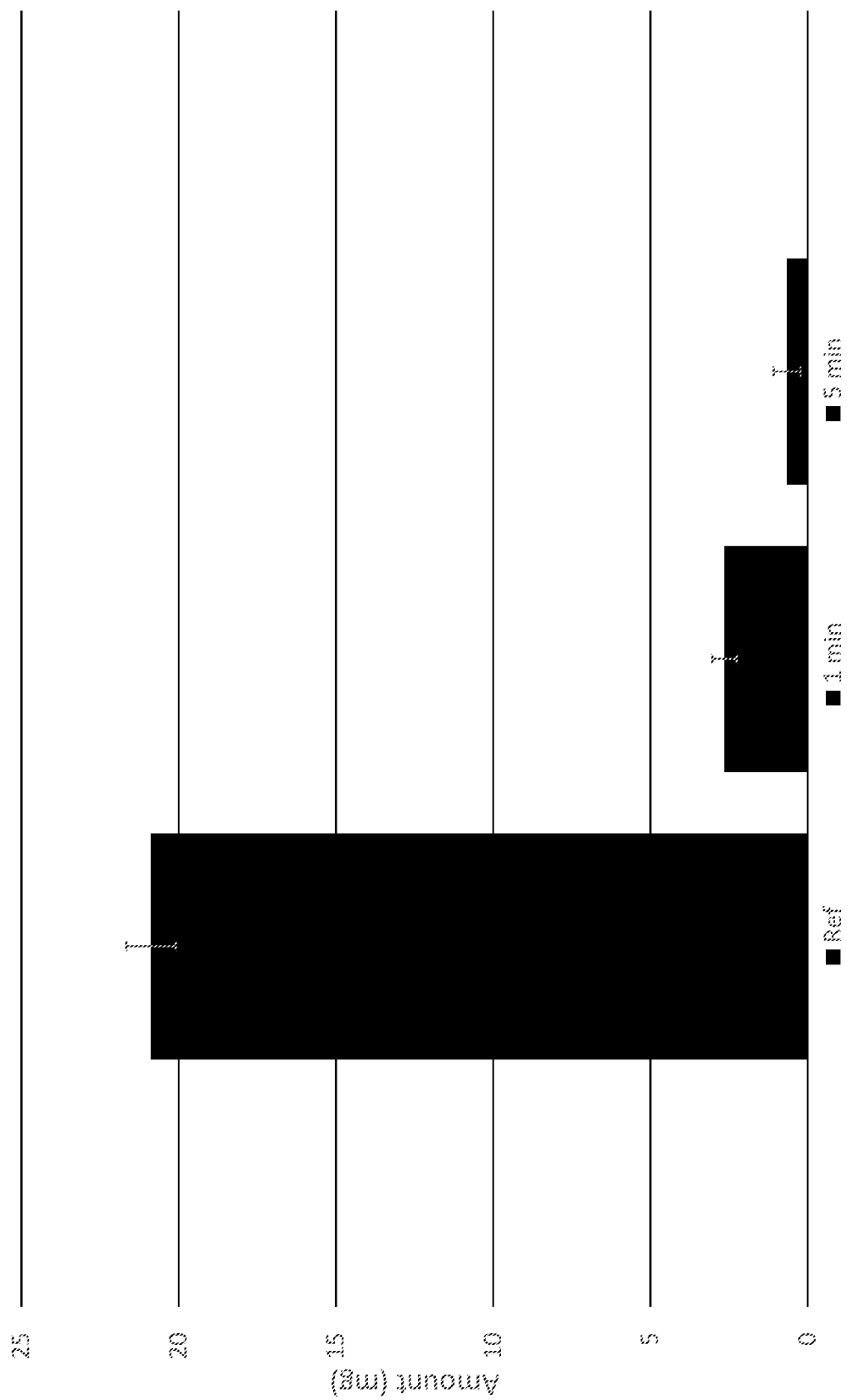
FIG. 4 shows the amount of nicotine in calcium sulphate rods before and after oven heat treatment (n=3)

Calcium sulphate rods were soaked in pure nicotine for 24 hours. The rods were able to absorb approximately 20 mg nicotine/rod. The amount of nicotine remaining in the rods after before and heat treatment was measured, and is shown in FIG. 4.

Most of the nicotine was released during heating. It was observed that a higher amount was released during 5 min of heating compared to 1 min of heating.

Figure 5:
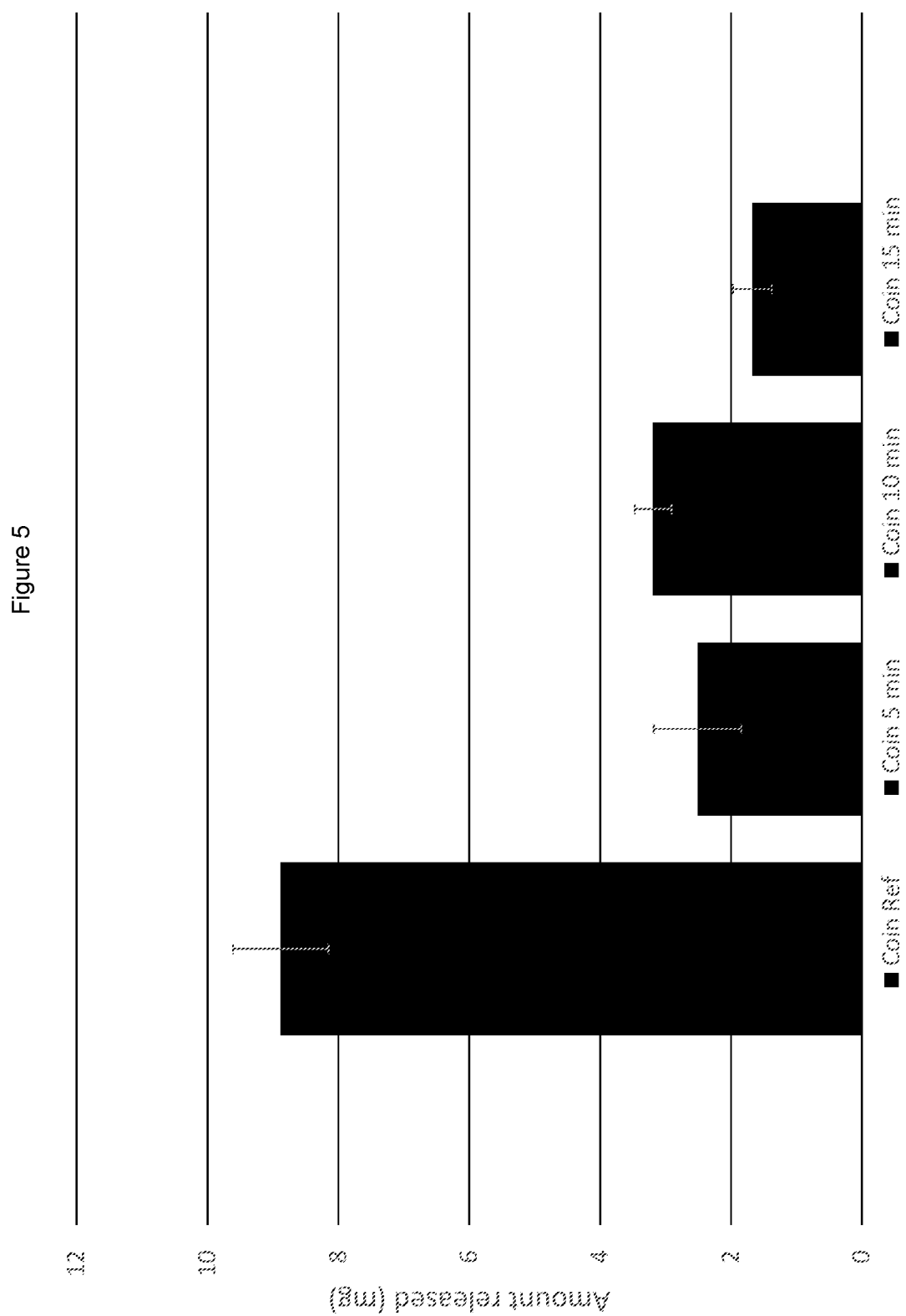
FIG. 5 shows the amount of nicotine in calcium sulphate coins before and after oven heat treatment (n=3)

Pure nicotine (20 mg) was dispensed onto calcium sulphate coins. The amount of nicotine remaining in the coins after before and heat treatment was measured, and is shown in FIG. 5.

Nicotine is a volatile substance and therefore the amount of nicotine detected in the reference sample was lower than 20 mg. Also in this case a lower release of nicotine was detected after heating.

Results—Geopolymer

Figure 6:
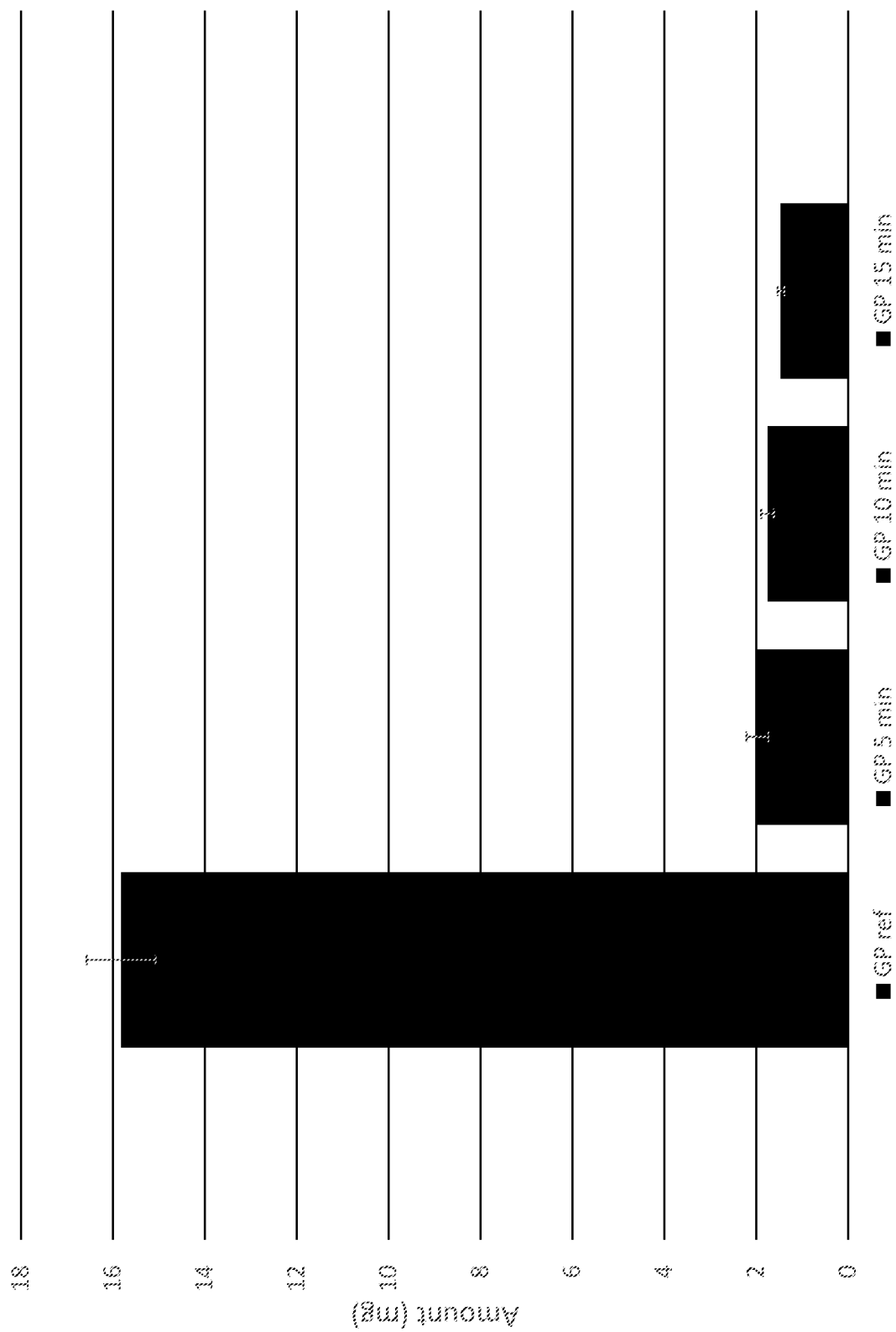
FIG. 6 shows the amount of nicotine in geopolymer coins before and after oven heat treatment (n=3)
Figure 7:
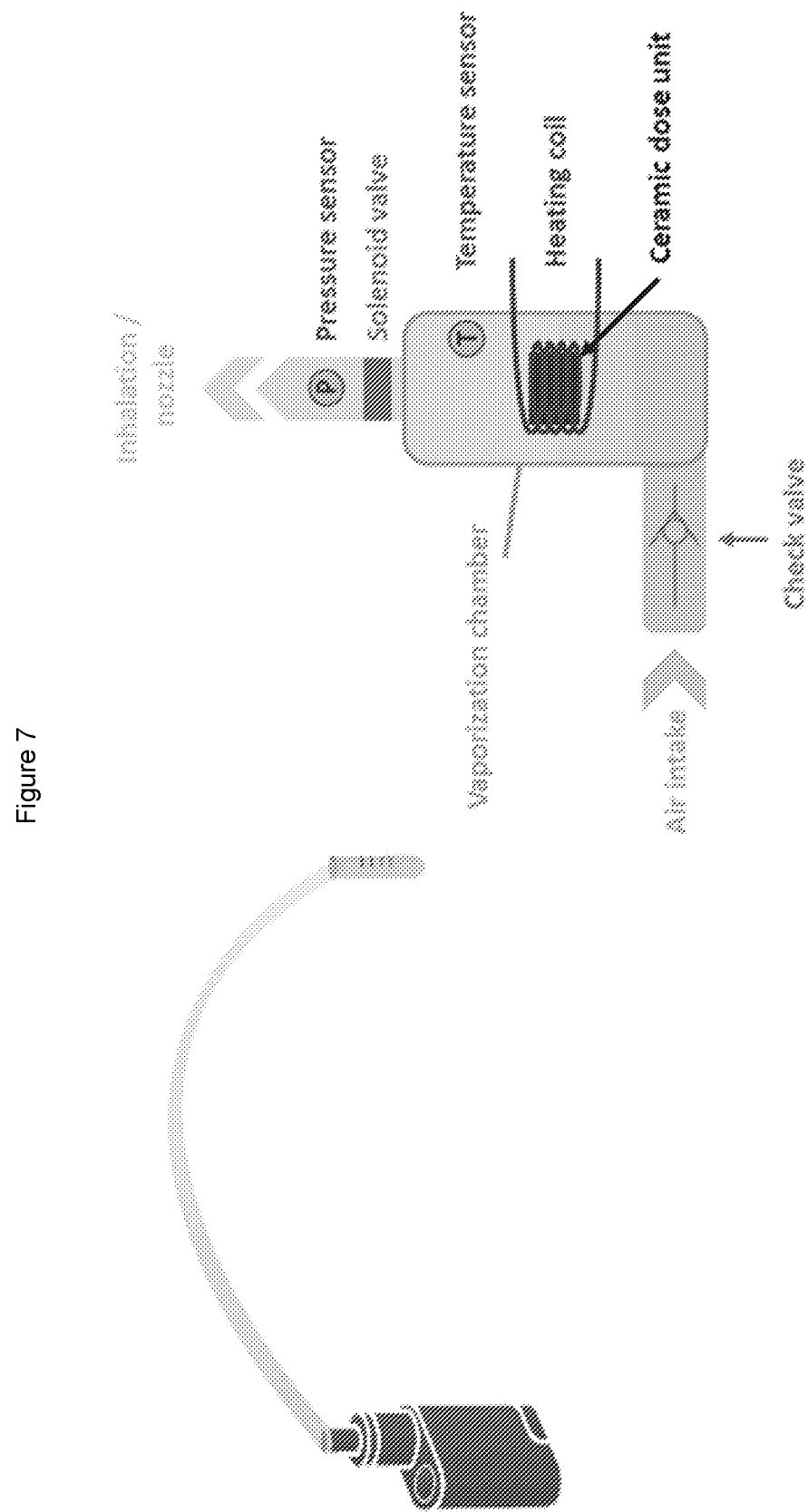
FIG. 7 shows the experimental setup for the e-cigarette device.

Pure nicotine (20 mg) was dispensed onto geopolymer coins. The amount of nicotine remaining in the coins after before and heat treatment was measured, and is shown in FIG. 6.

Nicotine is a volatile substance and therefore the amount of nicotine detected in the reference sample (about 16 mg) was less than that originally applied. Also in this case a lower release of nicotine was detected after heating.

Example 4

Heat Treatment Using an E-Cigarette Device

Materials

Aluminium oxide ceramic rods and calcium sulphate rods were obtained as described in Example 3. Nicotine and nicotine solutions were supplied and applied, and nicotine levels were detected as described in Example 3.

Heating Apparatus

Samples were heated using a prototype e-cigarette device (X-Cube II, Smoke) obtained from Devex Mekatronik AB (Sweden). The device is derived from the commercially available e-cigarette X-Cube.

Method

The sample in the device was heated up by a coil that is wrapped around the sample. The setting for the e-cigarette are listed in the table below.

TABLE

| Settings for e-cigarette device Setting for E-cigarette | |
| --- | --- |
| Maximum temperature | 315° C. |
| Maximum power | 6 W |
| Coil | Nickel |

The end of the device was connected to a vial via a silicon hose. The vial contained 1 ml of deionised water. To simulate smoking a rod was put into the device and puffing was performed. Puffing involves a sequence of 5 puffs that are each 10 seconds long. After puffing, the hose was removed and flushed with the water. The water was analysed for concentration of nicotine.

Results—Calcium Sulphate

Figure 8:
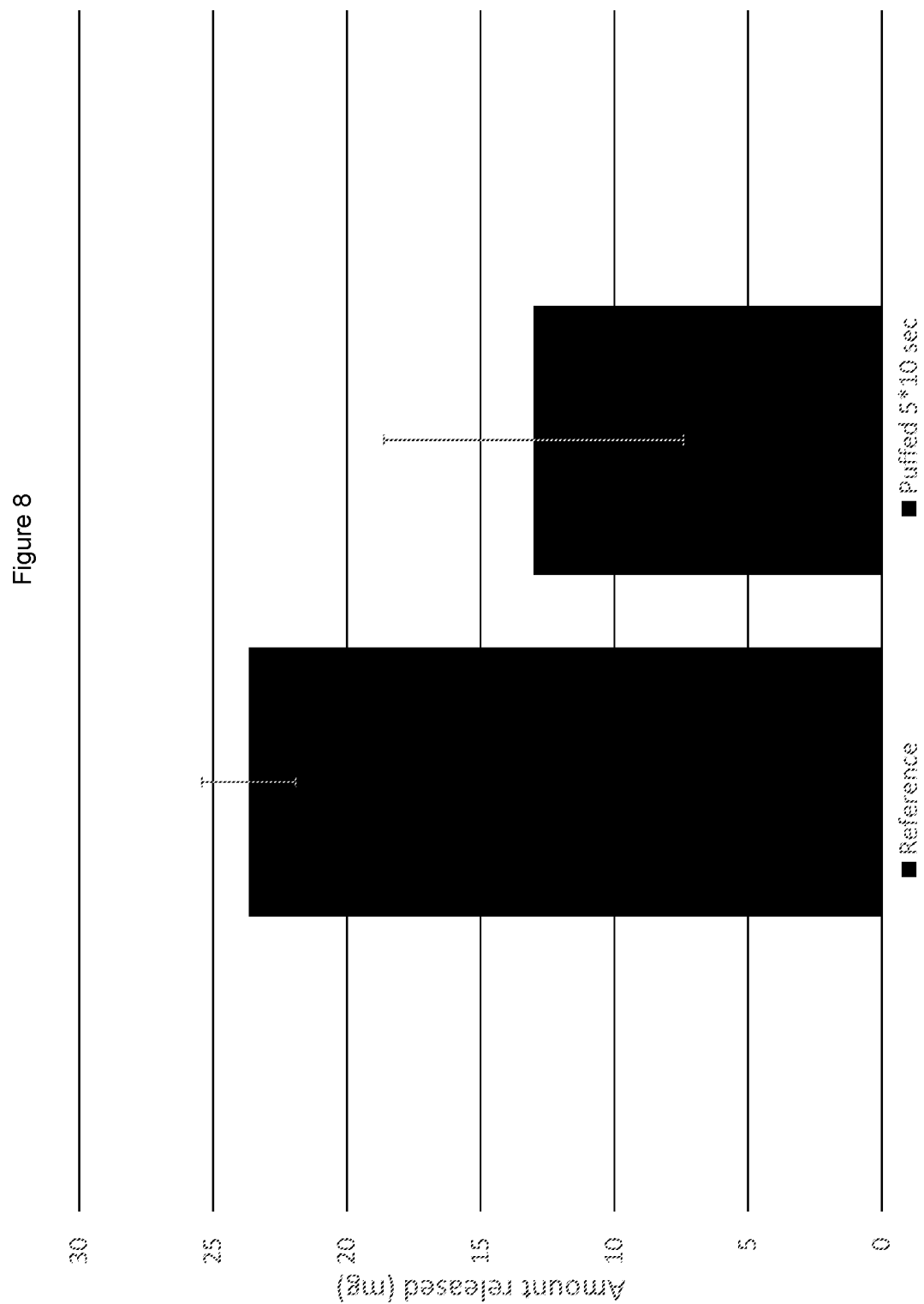
FIG. 8 shows the amount of nicotine in calcium sulphate rods before and after heat treatment in an e-cigarette device (n=3)

Calcium sulphate rods were soaked for 24 hours in pure nicotine and heated (5*10 sec.) in the e-cigarette device. The amount of nicotine remaining in the rods after before and heat treatment was measured, and is shown in FIG. 8.

The results show that a heat treatment in the device will result in a nicotine release.

Results—Aluminium Oxide

Figure 9:
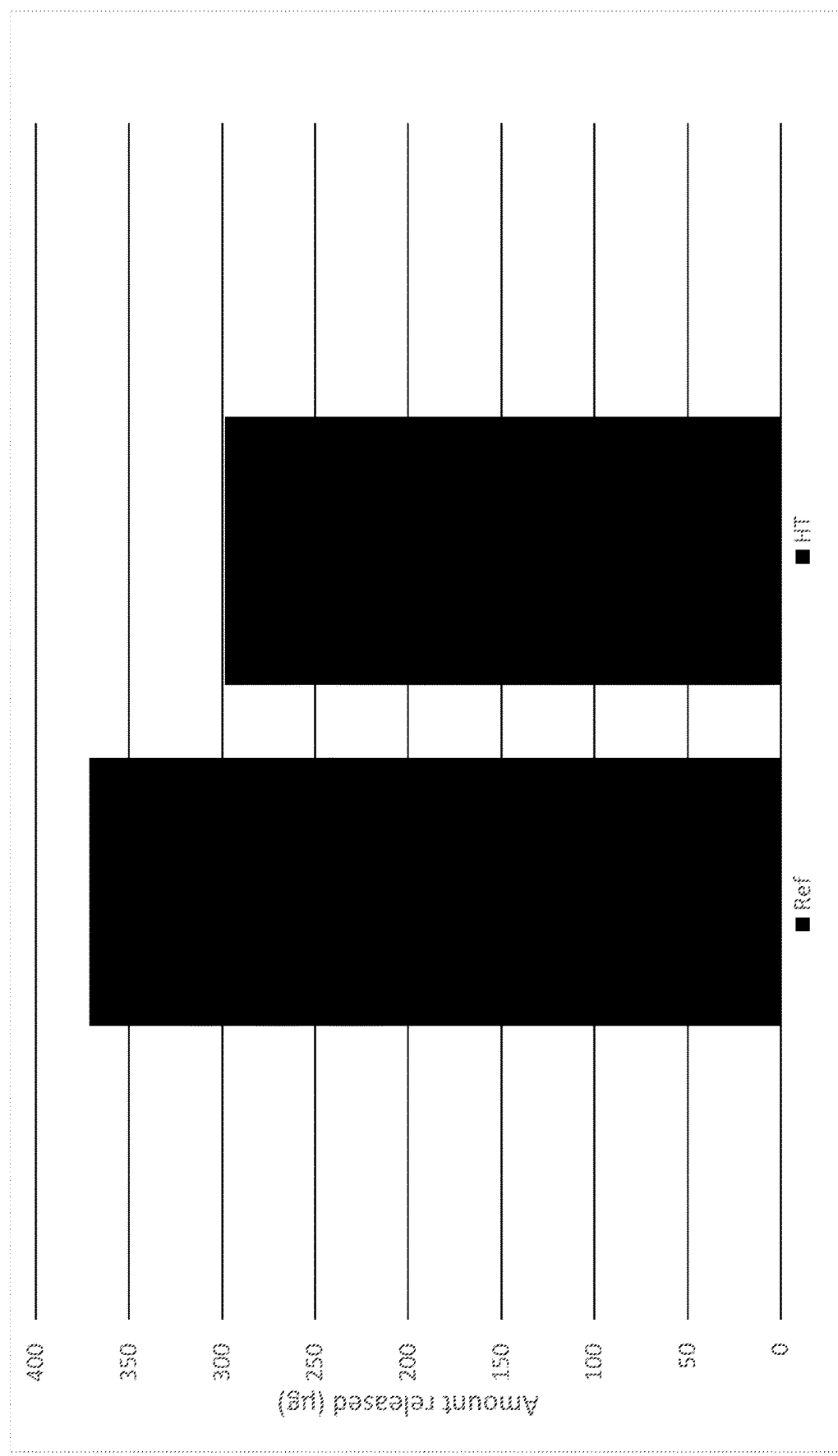
FIG. 9 shows the amount of nicotine in aluminium oxide rods before and after heat treatment in an e-cigarette device (n=3)

Aluminium oxide ($Al_2O_3$) rods were soaked for 24 hours in nicotine solution (18 mg/ml) and heated (5*10 sec.) in the device. The amount of nicotine remaining in the rods after before and heat treatment was measured, and is shown in FIG. 9.

Example 5

Heat Treatment Using Induction Heating

Materials

Calcium sulphate coins were obtained as described in Example 3. For the indirect induction test a magnet was molded into the coin. Nicotine and nicotine solutions were supplied and applied, and nicotine levels were detected as described in Example 3.

Heating Apparatus

Metal plate for induction cooker was obtained from Haneström (Sweden). Induction cooker Wilfa ICP-2000 was obtained from Media Markt (Sweden). Magnets (10*1 mm, Samarium Cobalt magnets, 0.4 kg pull) were obtained from first4magnets (UK). IR-thermometer (MS6520A) was obtained from Mastech (USA).

Heating Method

Figure 10:
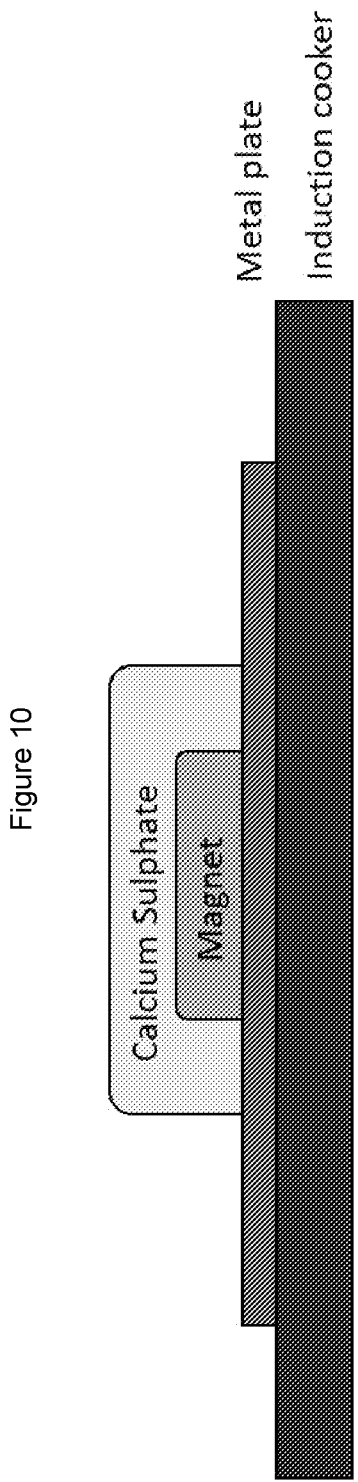
FIG. 10 shows the experimental setup for the induction tests.

Heat treatment by indirect induction was carried out by placing a metal plate onto the induction cooker. The ceramic coins containing a magnet was applied onto the metal plate and heated on maximum effect (exact temperature was not measured; see FIG. 10).

Results—Unheated Plate

Figure 11:
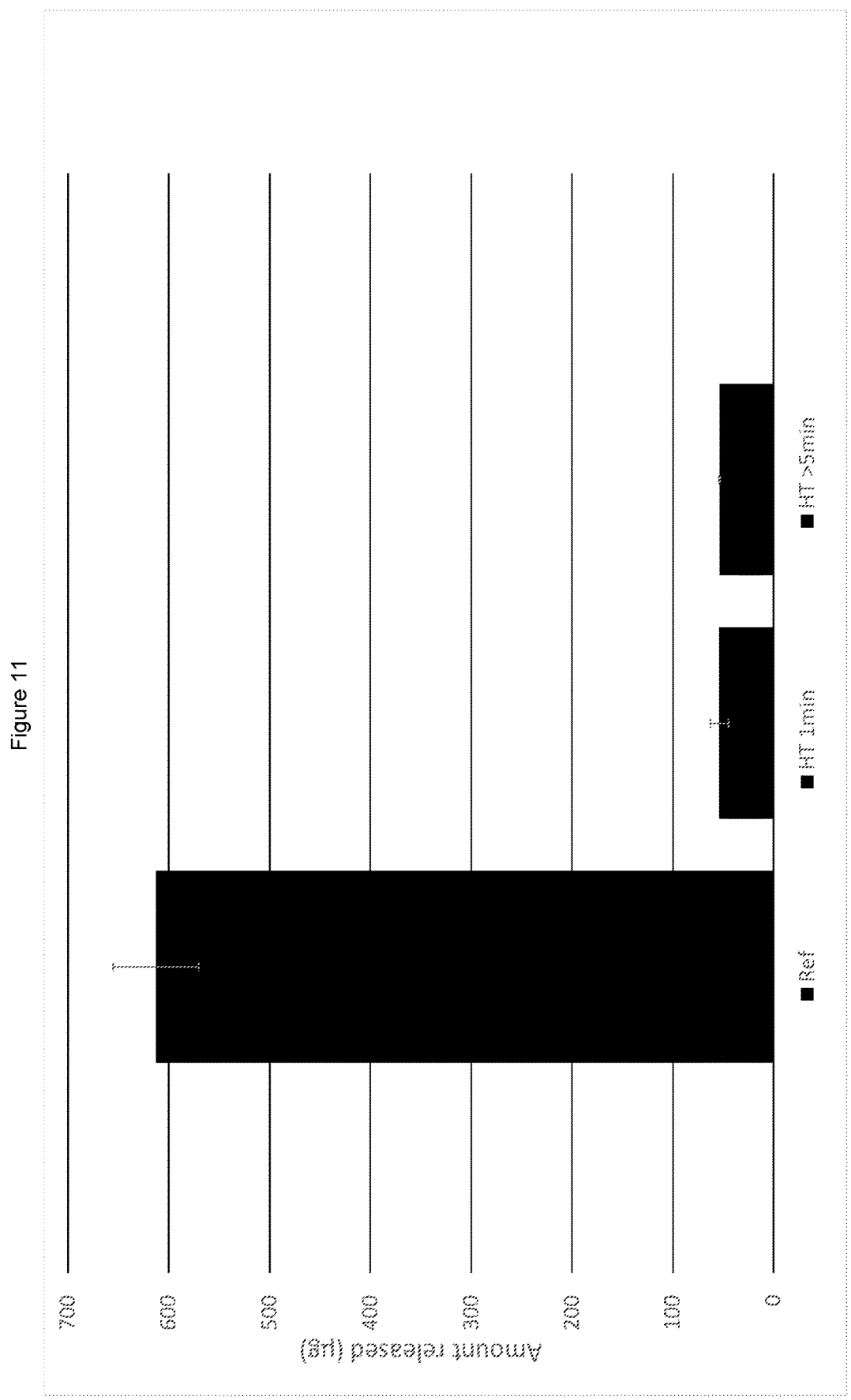
FIG. 11 shows the amount of nicotine in calcium sulphate coins before and after heat treatment using induction heating (n=3)

Nicotine solution (50μl, 18 mg/ml) was dispensed onto calcium sulphate coins and heated on an induction plate for about 1 minute or about 5 minutes. The amount of nicotine remaining in the coins after before and heat treatment was measured, and is shown in FIG. 11. Most of the nicotine was released within the first minute.

Results—Pre-Heated Plate

Figure 12:
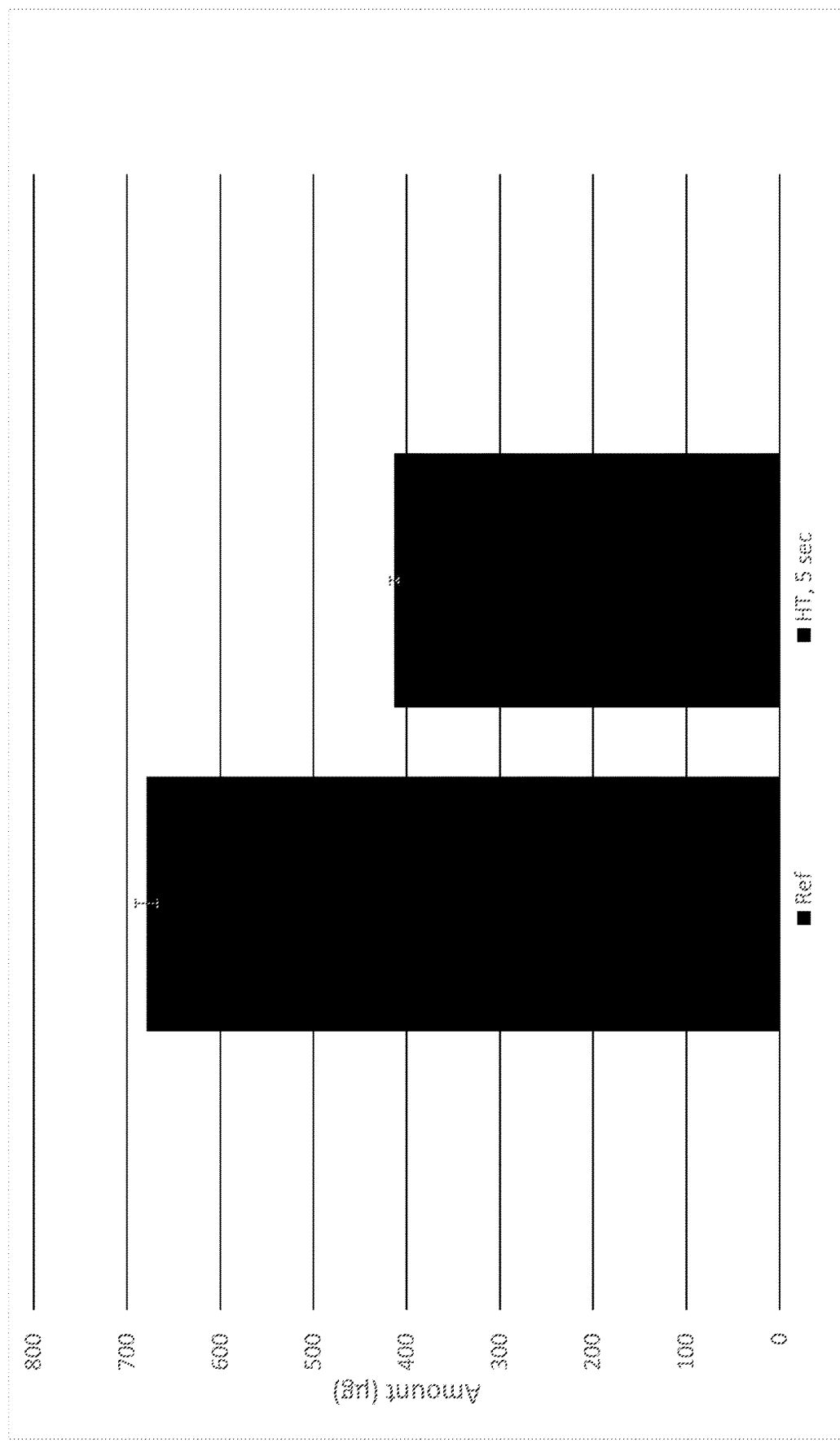
FIG. 12 shows the amount of nicotine in calcium sulphate coins before and after heat treatment using induction heating on a pre-heated plate (n=3)

Nicotine solution (50μl, 18 mg/ml) was dispensed onto calcium sulphate coins. The plate was preheated for approximately 10 seconds in order to obtain a high temperature (at least 150° C.). The coins were heated for 5 seconds on the plate before being taken off. The coins were set to cool down for approximately 15 minutes before putting into the extraction bath. The amount of nicotine remaining in the coins after before and heat treatment was measured, and is shown in FIG. 12.

The measurements show that a substantial quantity of nicotine was released as a result of the heat treatment.

Example 6

Sumatriptan Succinate

Materials

Aluminium oxide ceramic rods were obtained from Ceramtech (Sweden): $Al_2O_3$ cylindrical rods, 3 mm diameter and 10 mm length containing 4 bore holes (oriented axially) having a diameter of 0.8 mm. Sumatriptan succinate was obtained from SMS Pharmaceuticals Limited, India.

Application of Sumatriptan Succinate

The application of sumatriptan succinate was achieved by soaking the $Al_2O_3$ rods in a sumatriptan succinate solution with a concentration of 20 mg/ml. The volume of solution was around 100 μl but was not measured precisely; the volume was sufficient to fully immerse the rods. The samples were soaked for 24 hours in room temperature and thereafter the samples were dried for 24 hours, before heat treatment and/or analysis.

Heating Apparatus and Method

Oven Wilfa EMK 218 was obtained from Wilfa, (Norway). The temperature was set to approximately 300° C. The temperature was measured using an IR-thermometer from Mastech, USA. The rods were heated in the oven for a period of time ranging from 0 to 15 minutes.

Sumatriptan Succinate Detection

All sumatriptan release tests were carried out according to the same analytical method. The rods were immersed in a beaker containing 50 ml of deionised water. After 24 hours a sample of the water was taken out and filtered (pore size: 0.2 μm). The sample was characterized by UV-spectrophotometry at a wavelength of 282 nm. The amount sumatriptan succinate in the samples was then calculated. The reference samples represent the amount of sumatriptan succinate that was loaded before heat treatment. The difference between the amount of sumatriptan succinate detected in the heat-treated samples and the reference sample represents the amount of sumatriptan succinate that evaporated during the heat treatment.

Results

Figure 13:
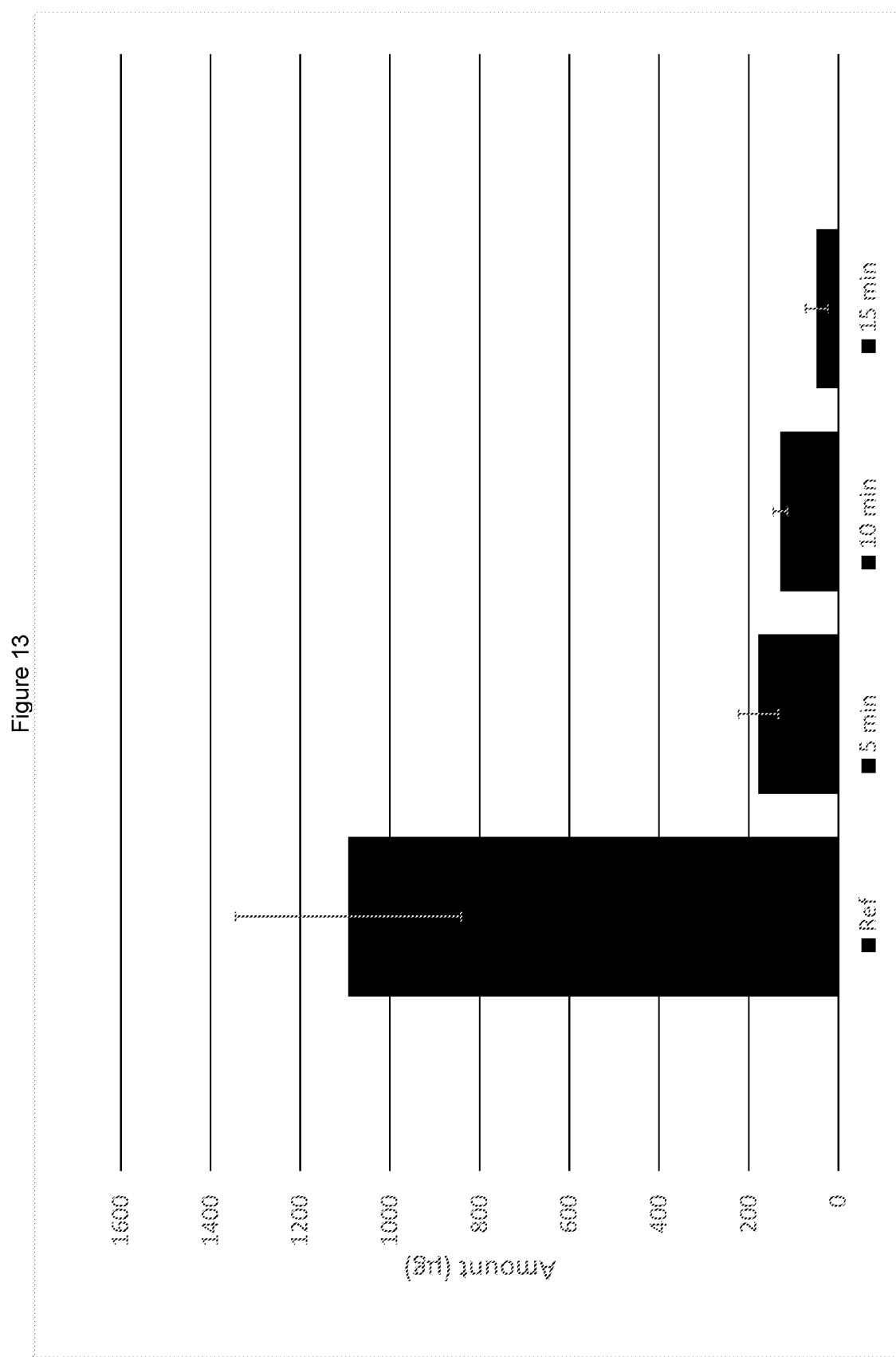
FIG. 13 shows the amount of sumatriptan succinate in $Al_2O_3$ rods before and after heat treatment using oven heating.

The amount of sumatriptan succinate remaining in the rods before and after heat treatment was measured, and is shown in FIG. 13.

When heated, almost all of the sumatriptan succinate was released within the first 5-15 minutes, since the amount of sumatriptan succinate remaining in the samples after heat treatment was low. The rods were able to absorb approximately 1 mg sumatriptan succinate/rod.

Example 7

Heating of Calcium Sulfate Coins Pre-Loaded with Clonidine Hydrochloride

Sample Preparation

Calcium sulphate alpha hemihydrate (CaS) was obtained from Bo Ehrlander AB (Sweden). Clonidine hydrochloride was obtained from PCAS (Finland). Shaped silicon rubbers were used as molds for coins (diameter: 12 mm, thickness: 2 mm). The calcium sulphate was mixed with powder of Clonidine hydrochloride (0.07 g Clonidine hydrochloride/g calcium sulphate) and deionised water (Liquid/Powder ratio of 0.4 (w/w)) to form a homogenous paste, which was used to fill the rubber molds. Once the paste had been applied, the molds were set to dry for at least 12 h under ambient conditions.

Heating Method

Oven Wilfa EMK 218 was obtained from Wilfa (Norway). The oven temperature was set to approximately 250° C. The temperature was measured using an IR-thermometer from Mastech (USA). The coins were heated in the oven for a period of time ranging from 0 to 15 minutes.

Clonidine Hydrochloride Release Detection

Each coin was weighed and immersed into a beaker containing 200 ml of deionised water. After 24 hours a sample of liquid was taken out and filtered (pore size: 0.2 μm). The sample was characterized by Shimadzu LC-2030 (Germany) HPLC system with a Genesis C18 analytical column 4 μm (100×2.1 mm i.d.) with a mobile phase of acetonitrile/phosphoric acid, pH 3 (11/89). The wavelength was set to 220 nm.

The reference samples represent the amount of clonidine hydrochloride mg/g calcium sulphate that was loaded before heat treatment. The difference in amount of clonidine hydrochloride detected in the heat-treated samples and the reference sample represents the amount of clonidine hydrochloride that evaporated during the heat treatment.

Results—Calcium Sulphate

Figure 14:
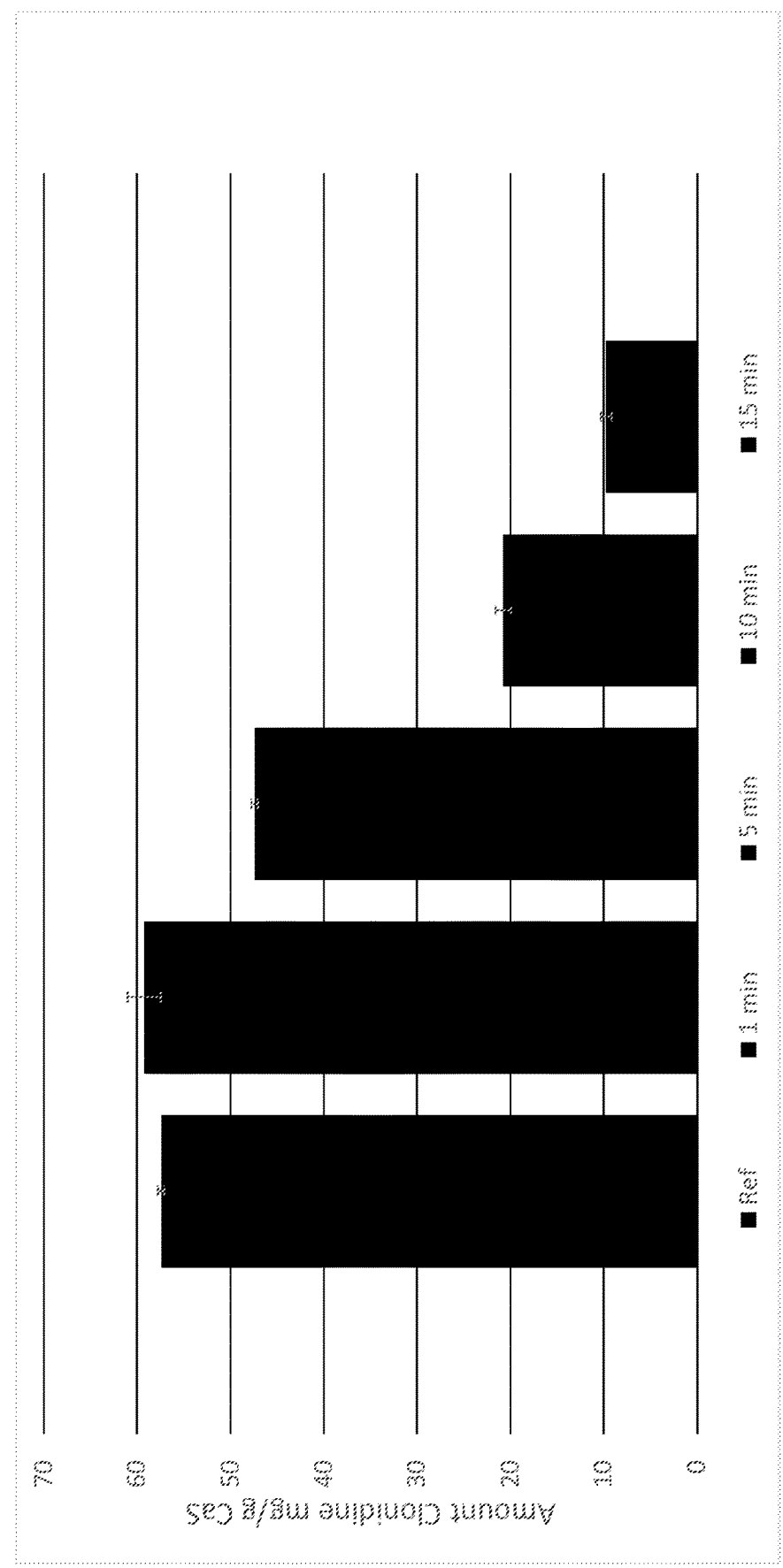
FIG. 14 shows the amount of clonidine hydrochloride in calcium sulphate coins before and after oven heat treatment (n=2)

Clonidine hydrochloride was mixed together with calcium sulphate (0.07 g clonidine hydrochloride/g Calcium sulphate) to form coins. The coins contained approximately 17 mg clonidine hydrochloride (1 coin weighed approximately 0.3 g). The coins were heated as described above (or not heated, in the case of the reference sample). The amount of clonidine hydrochloride remaining in the coins before and after heat treatment was measured, and is shown in FIG. 14. When heated, almost all of the clonidine hydrochloride was released within the first 15 mins, since the amount of clonidine hydrochloride remaining in the samples after heat treatment was low.

Example 8

Heating Calcium Sulfate Coins Loaded with Clonidine Hydrochloride

Sample Preparation

Calcium sulphate alpha hemihydrate (CaS) was obtained from Bo Ehrlander AB (Sweden). Clonidine hydrochloride was obtained from PCAS (Finland). Shaped silicon rubbers were used as molds for coins (diameter: 12 mm, thickness: 2 mm). The calcium sulphate was mixed with deionised water (Liquid/Powder ratio of 0.4 (w/w)) to form a homogenous paste, which was used to fill the rubber molds. When the paste was applied, the molds were set to dry for at least 12 h under ambient conditions.

Clonidine hydrochloride solution (50 µl, 5 mg/ml) was dispensed onto the calcium sulphate coins. When the solution was applied, the coins were set to dry for at least 12 h under ambient conditions.

Heating Method

Oven Wilfa EMK 218 was obtained from Wilfa, (Norway). The temperature was set to approximately 250° C. The temperature was measured using an IR-thermometer from Mastech, (USA). The coins were heated in the oven for a period of time ranging from 0 to 15 minutes.

Clonidine Hydrochloride Release Detection

Each coin was weighed and immersed into a beaker containing 200 ml of deionised water. After 24 hours a sample of the water was taken out and filtered (pore size: 0.2 µm). The sample was characterized by Shimadzu LC-2030 (Germany) HPLC system with a Genesis C18 analytical column 4 µm (100×2.1 mm i.d.) with a mobile phase of acetonitrile/phosphoric acid, pH 3 (11/89). The wavelength was set to 220 nm.

The reference samples represent the amount of clonidine hydrochloride that was loaded before heat treatment. The difference in amount of clonidine hydrochloride detected in the heat-treated samples and the reference sample represents the amount of clonidine hydrochloride that evaporated during the heat treatment.

Results—Calcium Sulphate

Figure 15:
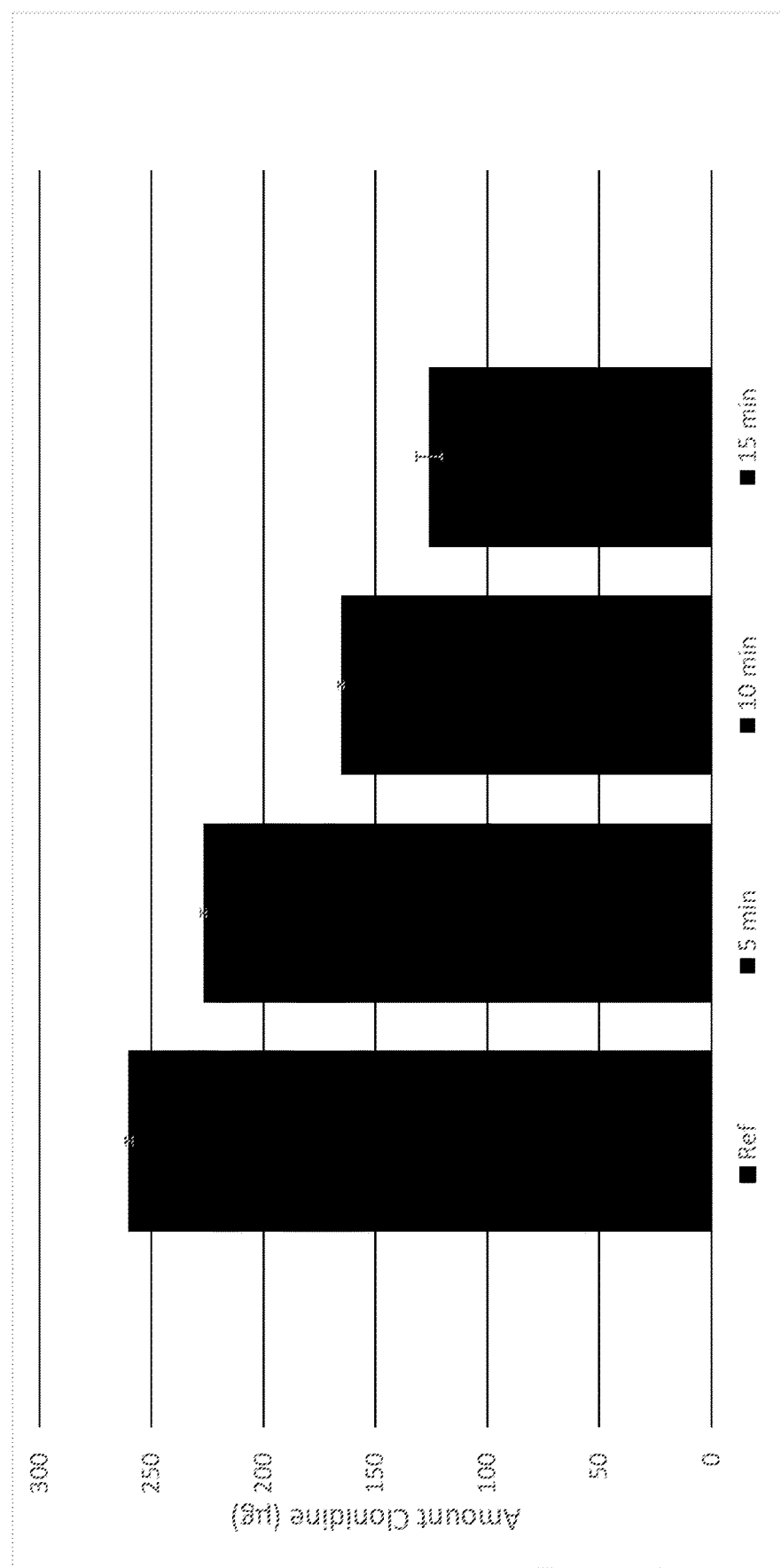
FIG. 15 shows the amount of clonidine hydrochloride in calcium sulphate coins before and after oven heat treatment (n=2)

Clonidine hydrochloride solution (50 µl, 5 mg/ml) was dispensed onto the calcium sulphate coins. The coins were heated as described above (or not heated, in the case of the reference sample). The amount of clonidine hydrochloride remaining in the coins before and after heat treatment was measured, and is shown in FIG. 15. During heating, the amount of clonidine hydrochloride present in the coins decreased significantly over time.

Example 9

Heating of Calcium Sulfate Coins Pre-Loaded with Nicotine

Sample Preparation

Calcium sulphate alpha hemihydrate (CaS) was obtained from Bo Ehrlander AB (Sweden). Shaped silicon rubbers were used as molds for coins (diameter: 12 mm, thickness: 2 mm). The calcium sulphate was mixed with a nicotine solution with a concentration of 5 or 20 mg/ml of nicotine (Liquid/Powder ratio of 0.4 (w/w)) to form a homogenous paste, which was filled in the rubber molds. Once the paste was applied, the molds were set to dry for at least 12 h under ambient conditions.

Heating Method

Oven Wilfa EMK 218 was obtained from Wilfa, (Norway). The temperature was set to approximately 200° C. The temperature was measured using an IR-thermometer from Mastech, (USA). The coins were heated in the oven for a period of time ranging from 0 to 15 minutes.

Nicotine Release Detection

Each coin was immersed into a beaker containing 50 ml of deionised water. After 24 hours a sample was taken out and filtered (pore size: 0.2 µm). The sample was characterized by UV-spectrophotometer at a wavelength of 219 nm. The amount nicotine in the samples were then calculated. The difference in amounts in the reference sample and the heat treated sample represents the amount of nicotine that evaporated during the heat treatment.

The reference samples represent the amount of nicotine µg/g calcium sulphate that was loaded before heat treatment. The difference in amount of nicotine detected in the heat-treated samples and the reference sample represents the amount of nicotine that evaporated during the heat treatment.

Results

Figure 16:
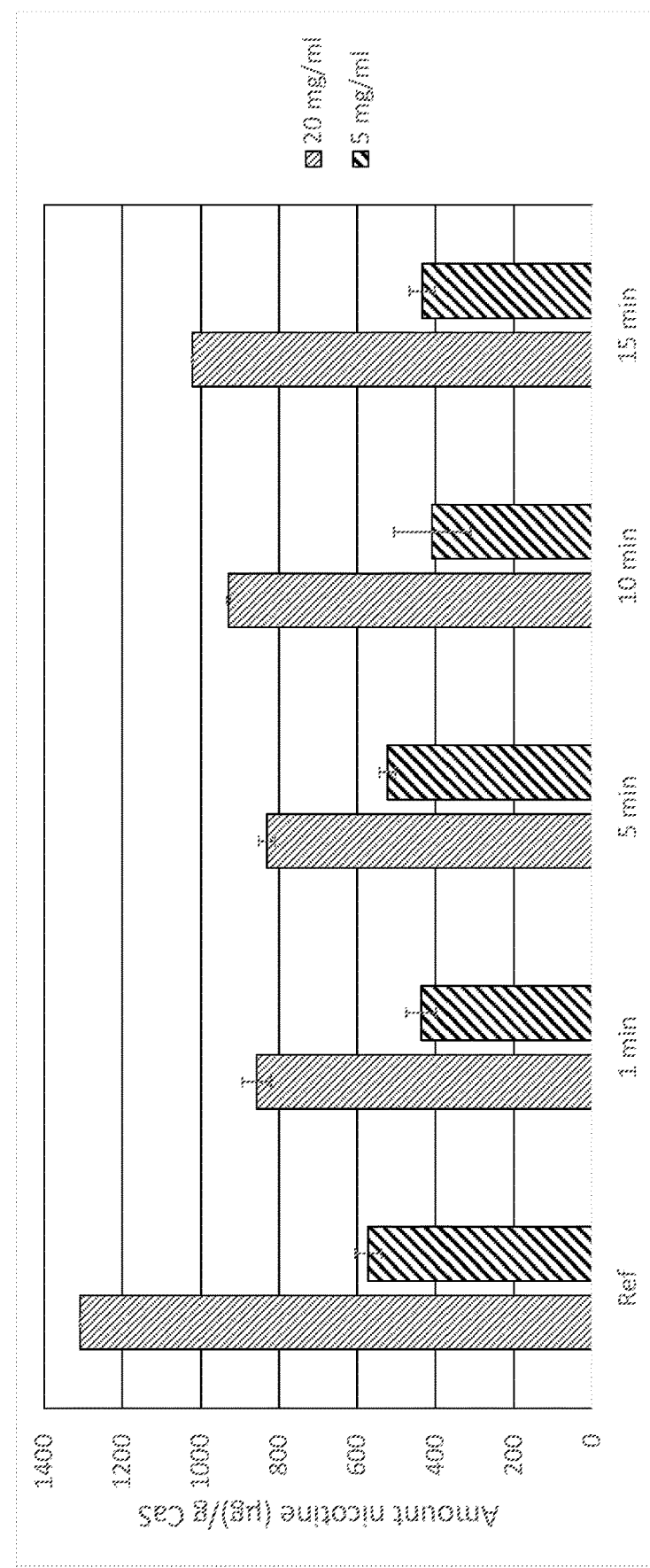
FIG. 16 shows the amount of nicotine in calcium sulphate coins before and after oven heat treatment (n=2)

Two different nicotine solutions were used to make coins; 5 mg/ml and 20 mg/ml. The same Liquid/Powder ratio of 0.4 (w/w) was used in both batches. The coins contained approximately 180 µg (for the coins mixed with 5 mg/ml nicotine solution) and 390 µg (for the coins mixed with 20 mg/ml nicotine solution). The amount of nicotine remaining in the coins before and after heat treatment was measured, and is shown in FIG. 16.

Example 10

Heating Calcium Sulfate Coins Pre-Loaded with Sumatriptan Succinate

Sample Preparation

Calcium sulphate alpha hemihydrate (CaS) was obtained from Bo Ehrlander AB (Sweden). Sumatriptan succinate was obtained from SMS Pharmaceuticals Limited, India. Shaped silicon rubbers were used as molds for coins (diameter: 12 mm, thickness: 2 mm). The calcium sulphate was mixed with sumatriptan succinate (0.07 g sumatriptan succinate/g calcium sulphate) and deionised water (Liquid/Powder ratio of 0.4 (w/w)) to form a homogenous paste, which was filled in the rubber molds. When the paste was applied, the molds were set to dry for at least 12 h under ambient conditions.

Heating Method

Oven Wilfa EMK 218 was obtained from Wilfa, (Norway). The temperature was set to approximately 250° C. The temperature was measured using an IR-thermometer from Mastech, (USA). The coins were heated in the oven for a period of time ranging from 0 to 15 minutes.

Sumatriptan Succinate Detection

The coins were immersed in a beaker containing 50 ml of deionised water. After 24 hours a sample of the water was taken out and filtered (pore size: 0.2 μm). The sample was characterized by UV-spectrophotometry at a wavelength of 282 nm. The amount Sumatriptan succinate in the samples was then calculated.

The reference samples represent the amount of Sumatriptan succinate that was loaded before heat treatment. The difference between the amount of Sumatriptan succinate detected in the heat-treated samples and the reference sample represents the amount of Sumatriptan succinate that evaporated during the heat treatment.

Results

Figure 17:
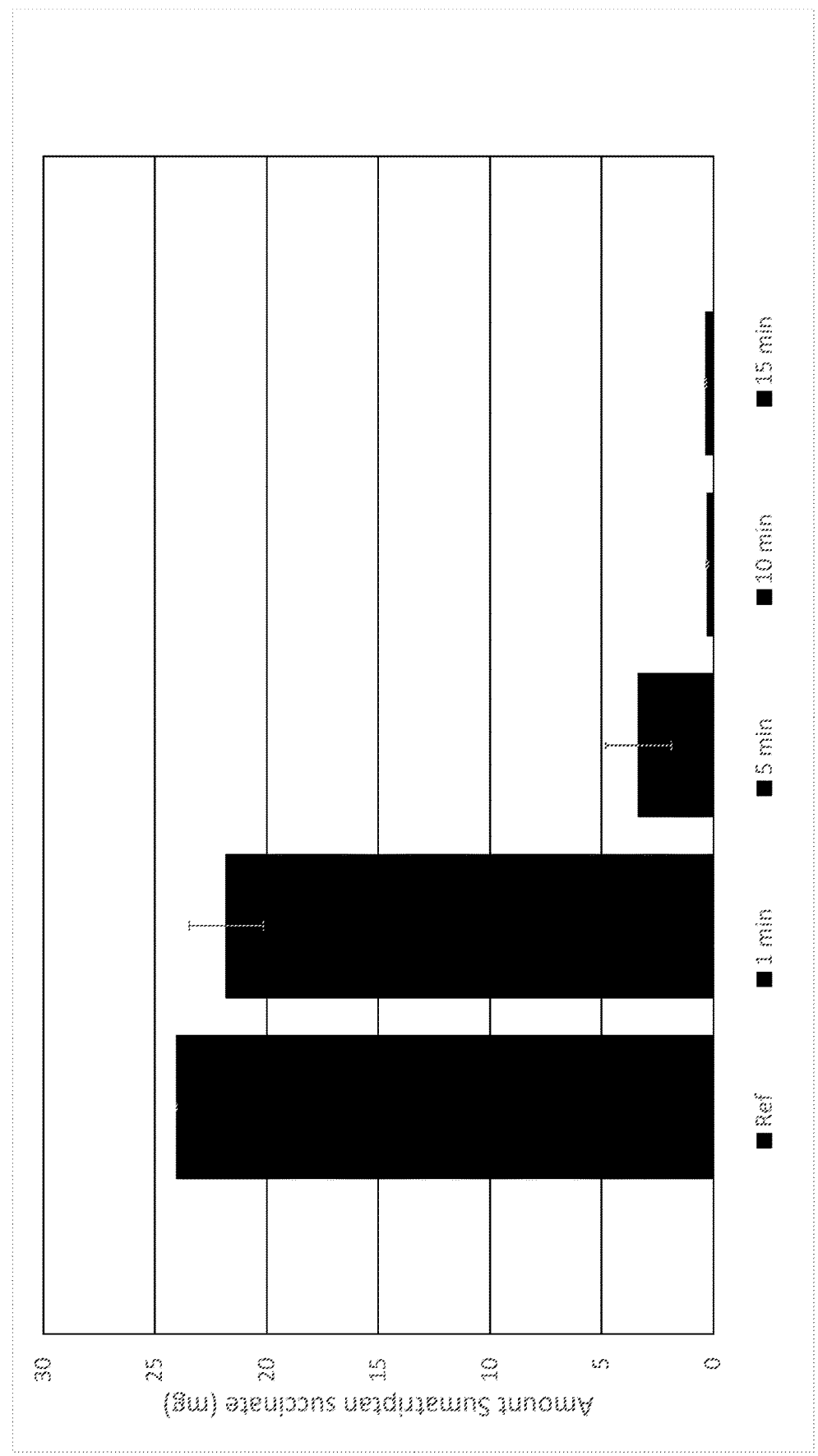
FIG. 17 shows the amount of sumatriptan succinate in calcium sulphate coins before and after oven heat treatment (n=2).

The amount of sumatriptan succinate remaining in the coins before and after heat treatment was measured, and is shown in FIG. 17. When heated, almost all of the Sumatriptan succinate was released within the first 15 mins, since the amount of Sumatriptan succinate remaining in the samples after heat treatment was low.

The invention claimed is:

1. A device for delivering a deliverable agent in the form of an aerosol or vapor to a user, the device comprising a solid, porous carrier material based on: (a) one or more chemically bonded ceramic materials, wherein the porous carrier material based on the one or more chemically bonded ceramic materials is not glass or (b) one or more geopolymeric materials, and having a porosity of at least 10%, and a deliverable agent located within the pores of the carrier material, wherein the device is operable to heat the carrier material and vaporize the deliverable agent, wherein the deliverable agent is an active pharmaceutical ingredient that is not nicotine or a salt thereof.

2. The device according to claim 1, wherein the solid, porous carrier material has a porosity of from about 20% to about 70%.

3. The device according to claim 1, wherein the average pore size in the carrier material is from about 0.1 μm to about 500 μm.

4. The device according to claim 1, wherein the deliverable agent is located predominantly within the pores of the carrier material.

5. The device according to claim 1, wherein the carrier material is selected from the list consisting of:
   (i) a material obtainable by the process of reacting an aluminosilicate precursor material with an aqueous alkaline liquid; and
   (ii) a calcium phosphate, a calcium sulfate, a calcium carbonate, a calcium silicate, a calcium aluminate, a magnesium carbonate, an aluminium silicate, and combinations thereof.

6. The device according to claim 1, wherein the carrier material is (i) a ceramic selected from the group consisting of, calcium sulfate, calcium phosphate, calcium silicate, calcium carbonate, calcium aluminate, magnesium carbonate, or a combination thereof, or (ii) a material obtainable by the process of reacting an aluminosilicate precursor material selected from the group consisting of kaolin, dickite, halloysite, nacrite, zeolites, illite, dehydroxylated zeolite, dehydroxylated halloysite, and metakaolin with an aqueous alkaline liquid.

7. The device according to claim 1, wherein the active pharmaceutical ingredient is an opioid analgesic or a non-steroidal anti-inflammatory drug (NSAID).

8. The device according to claim 7, wherein (a) the opioid analgesic is selected from morphine, oxycodone, buprenorphine, alfentanil, sufentanil, remifentanil and fentanyl or (b) the NSAID is selected from the group consisting of ibuprofen and aspirin.

9. The device according to claim 1, wherein the carrier material and the deliverable agent are provided together in a replaceable cartridge.

10. The device according to claim 9, wherein the replaceable cartridge consists essentially of the carrier material and the deliverable agent.

11. The device according to claim 1, further comprising a heating element operable to heat the carrier material.

12. The device according to claim 11, wherein the heating element is located proximally to the carrier material.

13. The device according to claim 1, wherein the device comprises a sufficient quantity of the active pharmaceutical ingredient to provide no more than one unit dosage of the active pharmaceutical ingredient to the user.

14. A method of delivering a deliverable agent in the form of a vapor or aerosol to a user, which method comprises:
   (a) providing a device comprising:
      (i) a solid, porous carrier material having a porosity of at least 10%; and
      (ii) a deliverable agent, wherein the deliverable agent is located within the pores of the carrier material and wherein the device is operable to heat the carrier material and vaporize the deliverable agent; and
   (b) heating the carrier material to vaporize the deliverable agent,
      wherein the carrier material is based on one or more chemically bonded ceramic materials or one or more geopolymeric materials, wherein the porous carrier material based on the one or more chemically bonded ceramic materials is not glass, and
      wherein the deliverable agent is an active pharmaceutical ingredient that is not nicotine or a salt thereof.

* * * * *